United States Patent
Kobayashi et al.

(10) Patent No.: US 9,572,501 B2
(45) Date of Patent: Feb. 21, 2017

(54) BLOOD PRESSURE INFORMATION MEASUREMENT DEVICE

(75) Inventors: Tatsuya Kobayashi, Shiga (JP); Kenji Fujii, Hyogo (JP); Hideaki Yoshida, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 891 days.

(21) Appl. No.: 13/567,525

(22) Filed: Aug. 6, 2012

(65) Prior Publication Data

US 2012/0302901 A1  Nov. 29, 2012

Related U.S. Application Data

(63) Continuation of application No. PCT/JP2011/052389, filed on Feb. 4, 2011.

(30) Foreign Application Priority Data

Feb. 26, 2010 (JP) ................................ 2010-042790

(51) Int. Cl.
*A61B 5/02* (2006.01)
*A61B 5/022* (2006.01)
(Continued)

(52) U.S. Cl.
CPC ........... *A61B 5/02233* (2013.01); *A61B 5/022* (2013.01); *A61B 5/0235* (2013.01); *A61B 5/7203* (2013.01); *A61B 5/02225* (2013.01)

(58) Field of Classification Search
CPC ... A61B 5/021; A61B 5/0205; A61B 5/02233; A61B 5/02225; A61B 5/022
(Continued)

(56) References Cited

U.S. PATENT DOCUMENTS 4,572,205 A * 2/1986 Sjonell ............... A61B 5/02233
600/499
6,338,718 B1 * 1/2002 Ogura .......................... 600/490
(Continued)

FOREIGN PATENT DOCUMENTS

JP  2000-316821 A  11/2000
JP  2004-113593 A   4/2004
(Continued)

OTHER PUBLICATIONS

Machine translation of JP2010-012164.*
(Continued)

*Primary Examiner* — Michael Kahelin
*Assistant Examiner* — Tho Tran
(74) *Attorney, Agent, or Firm* — Osha Liang LLP

(57) ABSTRACT

A blood pressure information measurement device includes a main body, including an inflation pump and an exhaust valve, and a cuff, including an air bladder for pulse wave measurement and an air bladder for blood pressure value measurement. The air bladder for pulse wave measurement and the air bladder for blood pressure value measurement are wrapped around a proximal side and a distal side of the upper arm, respectively. A first piping portion connects the air bladder for blood pressure value measurement to the inflation pump and the exhaust valve. A second piping portion branching from the first piping portion connects the air bladder for pulse wave measurement to the first piping portion. The second piping portion includes a 2-port valve that switches between connecting and disconnecting the air bladder for pulse wave measurement and the first piping portion, and a pressure sensor for measuring a pulse wave.

11 Claims, 16 Drawing Sheets

(51) Int. Cl.
*A61B 5/00* (2006.01)
*A61B 5/0235* (2006.01)

(58) Field of Classification Search
USPC .......................................................... 600/492
See application file for complete search history.

(56) References Cited

U.S. PATENT DOCUMENTS

| | | | | |
|---|---|---|---|---|
| 2004/0064055 | A1* | 4/2004 | Kawaguchi | .................... 600/490 |
| 2005/0234350 | A1* | 10/2005 | Sawanoi | ................ A61B 5/022 |
| | | | | 600/490 |
| 2007/0142731 | A1* | 6/2007 | Ye et al. | ........................ 600/494 |
| 2010/0324430 | A1* | 12/2010 | Inoue | ................. A61B 5/02116 |
| | | | | 600/493 |
| 2011/0077534 | A1* | 3/2011 | Kobayashi | ............... A61B 5/02 |
| | | | | 600/490 |

FOREIGN PATENT DOCUMENTS

| | | | |
|---|---|---|---|
| JP | 2004-195071 A | 7/2004 | |
| JP | 2007-044362 A | 2/2007 | |
| JP | 2007-522857 A | 8/2007 | |
| JP | 2009-284966 | * 10/2009 | ............... A61B 5/02 |
| JP | 2009-284965 A | 12/2009 | |
| JP | 2009-284966 A | 12/2009 | |
| JP | 2010-012164 A | 1/2010 | |
| WO | 2009145027 A1 | 12/2009 | |
| WO | 2010004840 A1 | 1/2010 | |

OTHER PUBLICATIONS

International Search Report issued in corresponding International Application No. PCT/JP2011/052389 dated Mar. 1, 2011 (2 pages).
Patent Abstracts of Japan, Publication No. 2000-316821, Published on Nov. 21, 2000, 1 page.
Patent Abstracts of Japan, Publication No. 2004-113593, Published on Apr. 15, 2004, 1 page.
Patent Abstracts of Japan, Publication No. 2007-044362, Published on Feb. 22, 2007, 1 page.
Patent Abstracts of Japan, Publication No. 2009-284965, Published on Dec. 10, 2009, 1 page.
Patent Abstracts of Japan, Publication No. 2009-284966, Published on Dec. 10, 2009, 1 page.
Patent Abstracts of Japan, Publication No. 2004-195071, Published on Jul. 15, 2004, 1 page.
Patent Abstracts of Japan, Publication No. 2010-012164, Published on Jan. 21, 2010, 1 page.

* cited by examiner

BLOOD PRESSURE INFORMATION MEASUREMENT DEVICE

TECHNICAL FIELD

The present invention relates to a blood pressure information measurement device that acquires blood pressure information by fitting a cuff provided with a fluid bag on a body, and more particularly to a blood pressure information measurement device configured to be capable of acquiring a pulse wave as blood pressure information.

BACKGROUND ART

Acquiring a test subject's blood pressure information is extremely important in finding out the condition of the test subject's health. In recent years, attempts have been made to capture cardiac load, degree of arteriosclerosis and the like by acquiring the pulse wave of a test subject, rather than only by acquiring systolic blood pressure value (hereinafter, maximum blood pressure), diastolic blood pressure value (hereinafter, minimum blood pressure) and the like whose usefulness as typical indices for health management has been widely recognized heretofore. A blood pressure information measurement device is a device for obtaining these indices for health management based on acquired blood pressure information, and further utilization in areas such as early detection, prevention and treatment of circulatory system diseases is anticipated. Note that blood pressure information includes a wide variety of information on the circulatory system, such as various indices and the like indicating systolic blood pressure value, diastolic blood pressure value, mean blood pressure value, pulse wave, pulse, and degree of arteriosclerosis.

Generally, a cuff is used in the measurement of blood pressure information. Here, a cuff denotes a belt-like or annular structure that contains a fluid bag having an inner cavity, and can be wrapped around a part of the body, and refers to a device that is used in the measurement of blood pressure information by inflating and deflating the fluid bag through injecting a fluid such as a gas or a liquid into the inner cavity. Note that a cuff used by being wrapped around an arm in particular is also called an armband or a manchette.

Conventionally, as blood pressure information measurement devices configured to be capable of acquiring an index indicating the degree of arteriosclerosis, devices are known that utilize the fact that the transmission velocity of a pulse wave ejected by the heart (hereinafter, pulse wave velocity (PWV)) increases as arteriosclerosis advances, and acquire an index indicating the degree of arteriosclerosis based on the measured PWV.

One such known blood pressure information measurement device is configured so that a cuff and a sensor are fitted on two or more measurement sites selected from the four limbs, the neck and the like, pulse waves are acquired simultaneously with the fitted cuff and sensor, PWV is measured based on the appearance time lag of the acquired pulse waves and the artery length between the measurement sites, and an index indicating the degree of arteriosclerosis is acquired based on the measured PWV.

As for the PWV measured in the abovementioned blood pressure information measurement devices, brachial-ankle pulse wave velocity (baPWV) and carotid-femoral pulse wave velocity (cfPWV) are typical. baPWV is the PWV measured as a result of the upper arm and ankle being selected as measurement sites, and a device disclosed in JP 2000-316821A is an example of a blood pressure information measurement device configured to be capable of acquiring an index indicating the degree of arteriosclerosis based on baPWV. Also, cfPWV is the PWV measured as a result of the neck and thigh being selected as measurement sites.

However, with a blood pressure information measurement device such as described above that measures baPWV or cfPWV and acquires an index indicating the degree of arteriosclerosis based on the acquired PWV, because the PWV needs to be measured after fitting the cuff and sensor to a plurality of sites on the body, the device may become comparatively large and the device constitution may be comparatively complex. Thus, even if these blood pressure information measurement devices can be used in a medical facility or the like, the reality at present is that these devices cannot readily be used in the home.

Thus, a blood pressure information measurement device configured so as to measure PWV after cuffs have been fitted on different positions of the upper arm, and acquire an index indicating the degree of arteriosclerosis based on the measured PWV is disclosed in JP 2004-113593A, so as to enable the device to be configured compactly.

The blood pressure information measurement device disclosed in JP 2004-113593A is configured such that cuffs are fitted to different positions on the upper arm, with an air bladder for occlusion contained in the cuff fitted on the distal side and an air bladder for pulse wave measurement contained in the cuff fitted on the proximal side, and a pulse wave is detected using the air bladder for pulse wave measurement in the state where the artery is occluded using the air bladder for occlusion, PWV is measured based on the time lag at which the peak value of an ejection wave component and the peak value of a reflective wave component included in the detected pulse wave appear and the artery length between the different positions of the upper arm on which the cuffs are fitted, and an index indicating the degree of arteriosclerosis based on the measured PWV is acquired. Here, an ejection wave is the pulse wave transmitted from the proximal side to the portion of the artery on which the air bladder for pulse wave measurement is fitted, and a reflective wave is the pulse wave transmitted from the distal side to the portion of the artery on which the air bladder for pulse wave measurement is fitted as a result of the ejection wave being reflected at the portion on which the air bladder for occlusion is fitted.

However, because two cuffs still need to be fitted even with the blood pressure information measurement device disclosed in the abovementioned JP 2004-113593A, it cannot be said that sufficient miniaturization has been achieved, and further miniaturization is needed to use the device in the home.

In view of this, a blood pressure information measurement device configured so as to measure PWV after a single cuff has been fitted on the upper arm, and to acquire an index indicating the degree of arteriosclerosis based on the measured PWV is disclosed in JP 2007-044362A, so as to enable the device to also be used in the home.

The blood pressure information measurement device disclosed in JP 2007-044362A is configured such that one large-volume air bladder for blood pressure value measurement and two small-volume air bladders for pulse wave measurement are contained in a cuff that is wrapped around the upper arm, and in the fitted state, one of the air bladders for pulse wave measurement is disposed on the proximal side of the air bladder for blood pressure value measurement and the other air bladder for pulse wave measurement is disposed on the distal side of the air bladder for blood pressure value measurement, blood pressure values are measured using the air bladder for blood pressure value measurement, and PWV is measured based on the appearance time lag of the pulse waves detected using the two air bladders for pulse wave measurement and the distance between these two air bladders for pulse wave measurement, and an index indicating the degree of arteriosclerosis is acquired based on the measured PWV.

However, with the blood pressure information measurement device disclosed in the abovementioned JP 2007-044362A, because the device is configured to detect the pulse wave using the two air bladders for pulse wave measurement without occluding the artery included at the fitting site of the cuff, the reflective wave from the artery positioned on the distal side of the fitting site will be superimposed on the pulse wave that is detected, making it difficult to appropriately separate the reflective wave, and resulting in a significant drop in PWV measurement accuracy. Thus, in the case where the blood pressure information measurement device is configured as disclosed in JP 2007-044362A, it is difficult to raise the accuracy of the index indicating the degree of arteriosclerosis that is acquired.

Blood pressure information measurement devices that have achieved device miniaturization to an extent that enables use in the home, and can, moreover, measure PWV with high accuracy, enabling an index indicating the degree of arteriosclerosis to be acquired with high accuracy as a result, are disclosed in JP 2009-284965A and JP 2009-284966A, for example.

The blood pressure information measurement devices disclosed in JP 2009-284965A and JP 2009-284966A are configured such that a single cuff is fitted on the upper arm, with one large-volume air bladder for blood pressure value measurement and one small-volume air bladder for pulse wave measurement contained in the cuff, and in the fitted state, the air bladder for pulse wave measurement is disposed on the proximal side of a fitting site, while the air bladder for blood pressure value measurement is disposed on the distal side of a fitting site, blood pressure values are measured with the air bladder for blood pressure value measurement, and a pulse wave is detected using the air bladder for pulse wave measurement while maintaining a state in which the artery is occluded using the air bladder for blood pressure value measurement, and PWV is measured based on the time lag at which the peak value of an ejection wave component and the peak value of a reflective wave component included in the detected pulse wave appear and the artery length from the heart (more specifically, subclavian artery bifurcation) to the iliac artery bifurcation, and an index indicating the degree of arteriosclerosis is acquired based on the measured PWV. Here, an ejection wave is the pulse wave that is transmitted directly from the heart to the portion of the artery on which the air bladder for pulse wave measurement is fitted, and a reflective wave is the pulse wave transmitted to the portion of the artery on which the air bladder for pulse wave measurement is fitted as a result of the ejection wave being reflected at the iliac artery bifurcation.

With the blood pressure information measurement devices disclosed in JP 2009-284965A and JP 2009-284966A, because a configuration is employed in which a single cuff is fitted on the upper arm, and one air bladder for blood pressure value measurement and one air bladder for pulse wave measurement are contained in a single cuff, and because the device can be miniaturized as compared with conventional technology, and the air bladder for blood pressure value measurement can also be used as a cuff for occluding an artery, pulse wave measurement can be performed in a state in which the distal side is occluded, enabling PWV to be measured with high accuracy, without the possibility of the reflective wave from an artery positioned on the distal side of the fitting site being superimposed on the pulse wave that is detected. The blood pressure information measurement devices disclosed in JP 2009-284965A and JP 2009-284966A can also be configured to inflate the air bladder for blood pressure value measurement and the air bladder for pulse wave measurement simultaneously or selectively using a single inflation pump, in which case, further miniaturization of the device and simplification of the device configuration will also be achieved.

Accordingly, if a blood pressure information measurement device as disclosed in JP 2009-284965A and JP 2009-284966A is employed, miniaturization of the device and simplification of the device configuration to an extent that enables use in the home is achieved, and, moreover, PWV can be measured with high accuracy, enabling an index indicating the degree of arteriosclerosis to be acquired with high accuracy as a result.

Note that JP 2009-284965A and JP 2009-284966A also describe being able to acquire an index indicating the degree of arteriosclerosis based on the difference, ratio or the like of an amplitude of the ejection wave component and an amplitude of the reflective wave component included in the detected pulse wave, besides the abovementioned acquisition of an index indicating the degree of arteriosclerosis based on PWV.

Also, in addition to JP 2009-284965A and JP 2009-284966A, JP 2004-195071A and JP 2007-522857A describe applying a higher compression force than maximum blood pressure to an artery when detecting a pulse wave, and performing various types of pulse wave analysis based on the pulse wave detected in that state, given that differences arise in the shape of the pulse waves detected in the case where the compression force at the time of compressing an artery differs.

Patent Literature 1 JP 2000-316821A
Patent Literature 2 JP 2004-113593A
Patent Literature 3 JP 2007-044362A
Patent Literature 4 JP 2009-284965A
Patent Literature 5 JP 2009-284966A
Patent Literature 6 JP 2004-195071A
Patent Literature 7 JP 2007-522857A

SUMMARY OF INVENTION

Incidentally, even in the case where blood pressure information measurement devices as disclosed in the abovementioned JP 2009-284965A and JP 2009-284966A are employed, because the fluctuation in the pulse wave to be detected is extremely minute, it is imperative that the device be configured such that the signal/noise (S/N) ratio of the pulse wave signal that is detected and output with a pressure sensor is raised sufficiently. Here, in the case where the S/N ratio of the pulse wave signal cannot be maintained high enough, the pulse wave can no longer be detected with high accuracy, which naturally results in no longer being able to acquire the index indicating the degree of arteriosclerosis obtained by analyzing the detected pulse wave with high accuracy.

Accordingly, one or more embodiments of the present invention provide a blood pressure information measurement device that is able to measure a pulse wave with high accuracy.

A blood pressure information measurement device according to one or more embodiments the present invention is provided with a cuff, a first fluid bag, a second fluid bag, an inflation/deflation mechanism, a piping, an opening/closing valve, a first pressure detection unit, and a pulse wave acquisition unit. The cuff takes an annular form in a fitted state of being fitted on a fitting site. The first fluid bag is provided in the cuff and is wrapped around a proximal side of the fitting site in the fitted state. The second fluid bag is provided in the cuff and is wrapped around a portion including a distal side of the fitting site in the fitted state. The inflation/deflation mechanism is capable of inflating/deflating the first fluid bag and the second fluid bag. The piping connects the first fluid bag and the second fluid bag to the inflation/deflation mechanism. The opening/closing valve is provided in the piping, and allows communication of the first fluid bag with at least one of the second fluid bag and the inflation/deflation mechanism in an open state and maintains an internal pressure of the first fluid bag by preventing communication of the first fluid bag with the second fluid bag and the inflation/deflation mechanism in a closed state. The first pressure detection unit is provided on a portion of the piping connecting the first fluid bag and the opening/closing valve, and detects the internal pressure of the first fluid bag. The pulse wave acquisition unit acquires a pulse wave based on the pressure detected by the first pressure detection unit. Here, the opening/closing valve is provided in the cuff, the portion of the piping connecting the first fluid bag and the opening/closing valve is also provided in the cuff, and the first pressure detection unit is also provided in the cuff.

With the blood pressure information measurement device according to one or more embodiments of the present invention, the piping includes a first piping portion that connects the inflation/deflation mechanism and the second fluid bag, and a second piping portion that branches from the first piping portion and connects the first piping portion and the first fluid bag. In this case, the opening/closing valve may be constituted by a 2-port valve provided in the second piping portion, or may be constituted by a 3-port valve provided at a connection point of the first piping portion and the second piping portion.

The blood pressure information measurement device according to one or more embodiments of the present invention is further provided with a second pressure detection unit that detects an internal pressure of the second fluid bag, and a blood pressure value acquisition unit that acquires a blood pressure value based on the pressure detected by the second pressure detection unit.

With the blood pressure information measurement device according to one or more embodiments of the present invention, the second fluid bag may cover an outer side of the first fluid bag, so as to be wrapped around substantially an entirety of the fitting site in the fitted state, or may be disposed alongside the first fluid bag in an axial direction of the cuff, so as to be wrapped around only a portion excluding the proximal side of the fitting site in the fitted state.

With the blood pressure information measurement device according to one or more embodiments of the present invention, the cuff further includes an outer body in which the first fluid bag and the second fluid bag are housed, in which case the opening/closing valve is housed in the outer body, the portion of the piping connecting the first fluid bag and the opening/closing valve is also housed in the outer body, and the first pressure detection unit is also housed in the outer body.

The blood pressure information measurement device according to one or more embodiments of the present invention may be further provided with a main body that is separate from the cuff, and in which the inflation/deflation mechanism is provided. In this case, the cuff and the main body may be connected via a portion of the piping and the portion of the piping connecting the cuff and the main body may be constituted by a flexible tube, or the cuff and the main body may be rotatably coupled.

The blood pressure information measurement device according to one or more embodiments of the present invention may be further provided with a curved elastic board that is provided in the cuff and is positioned on an outer side of the first fluid bag and the second fluid bag in the fitted state, and a third fluid bag that is provided in the cuff and is positioned on an outer side of the curve elastic board in the fitted state.

The blood pressure information measurement device according to one or more embodiments of the present invention is further provided with an index calculation unit that calculates an index indicating a degree of arteriosclerosis based on the pulse wave acquired by the pulse wave acquisition unit.

According to one or more embodiments of the present invention, a blood pressure information measurement device that is able to measure a pulse wave with high accuracy can be realized.

DETAILED DESCRIPTION OF INVENTION

Hereinafter, embodiments of the present invention will be described in detail with reference to drawings. In the description of the embodiments shown below, a blood pressure information measurement device provided with both a function of acquiring blood pressure values such as maximum blood pressure and minimum blood pressure and displaying these acquired values, and a function of detecting a pulse wave, acquiring an index indicating the degree of arteriosclerosis and displaying the acquired index is illustrated as an exemplary blood pressure information measurement device. Embodiment 1 shown below is an example of the case where the present invention is applied to a blood pressure information measurement device constituted by a separate main body and cuff, with the main body and cuff being connected via a flexible tube, and Embodiment 2 shown below is an example of the case where the present invention is applied to a blood pressure information measurement device constituted by a separate main body and cuff, with the main body and cuff being movably coupled. Note that in the embodiments shown below, the same reference signs are given to the same or equivalent portions, and description thereof will not be repeated.

Embodiment 1

Figure 1:
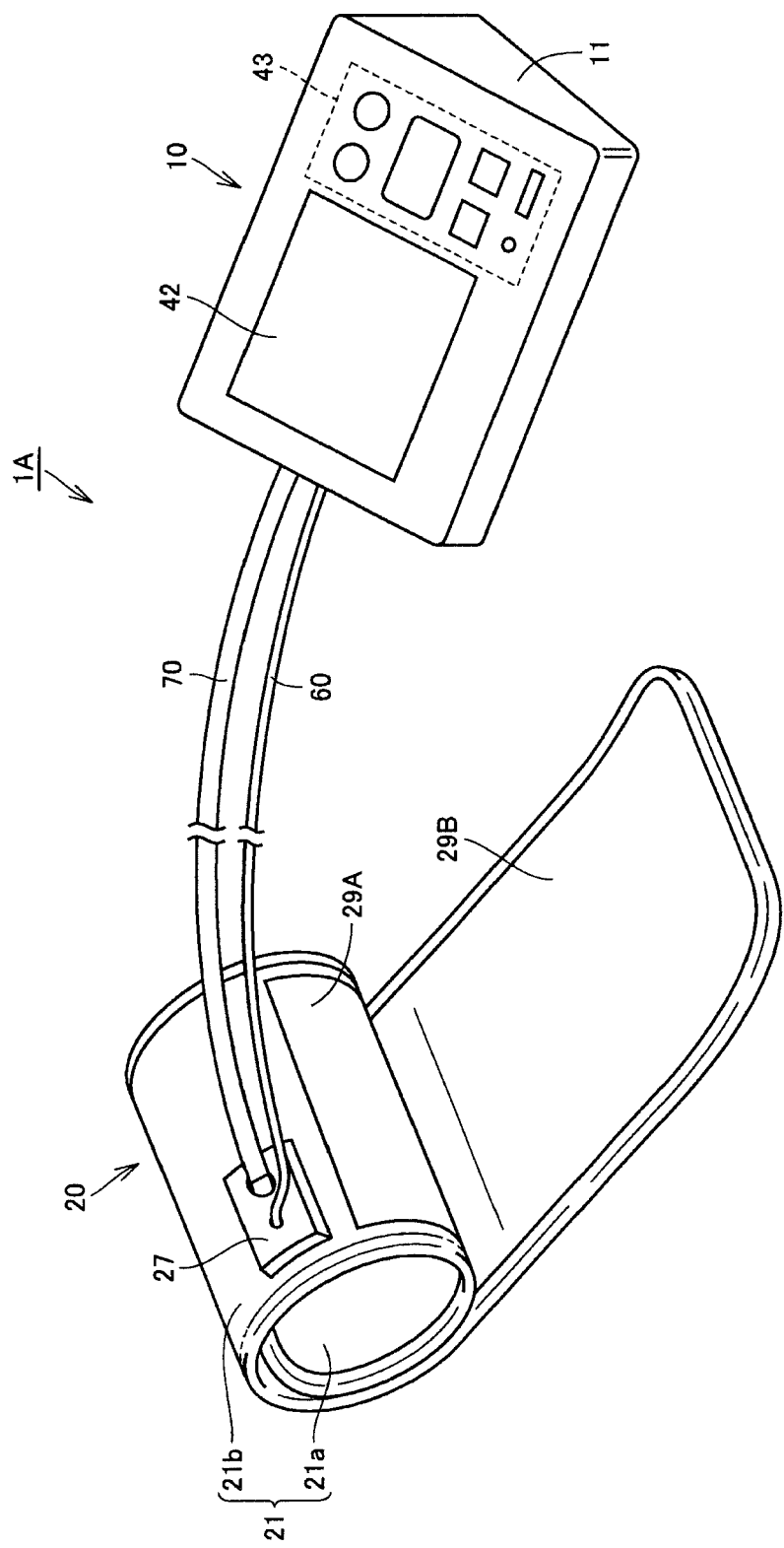
FIG. 1 is a perspective diagram showing an external structure of a blood pressure information measurement device in Embodiment 1 of the present invention.
Figure 2:
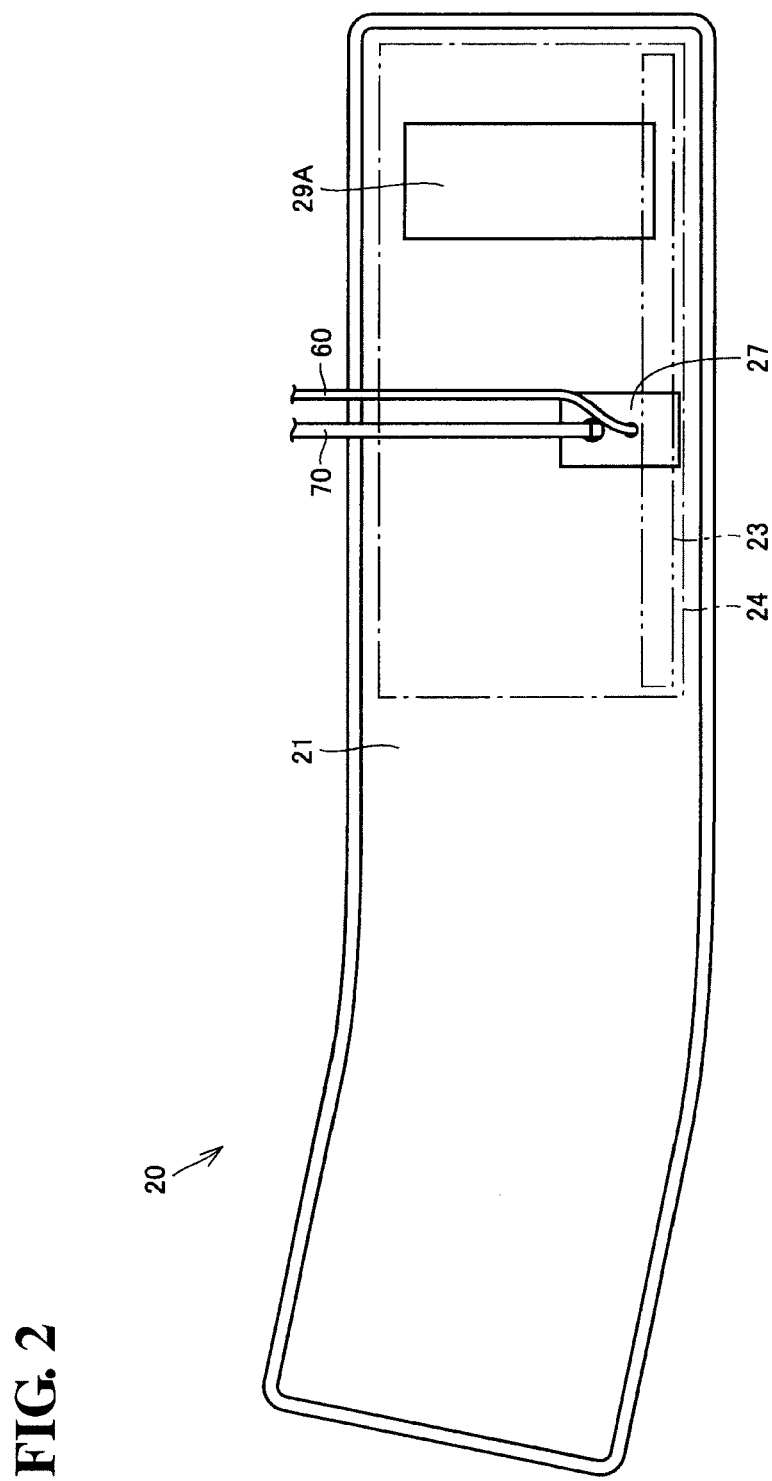
FIG. 2 is a development view of the cuff shown in FIG. 1 as seen from an outer circumferential surface side.
Figure 3:
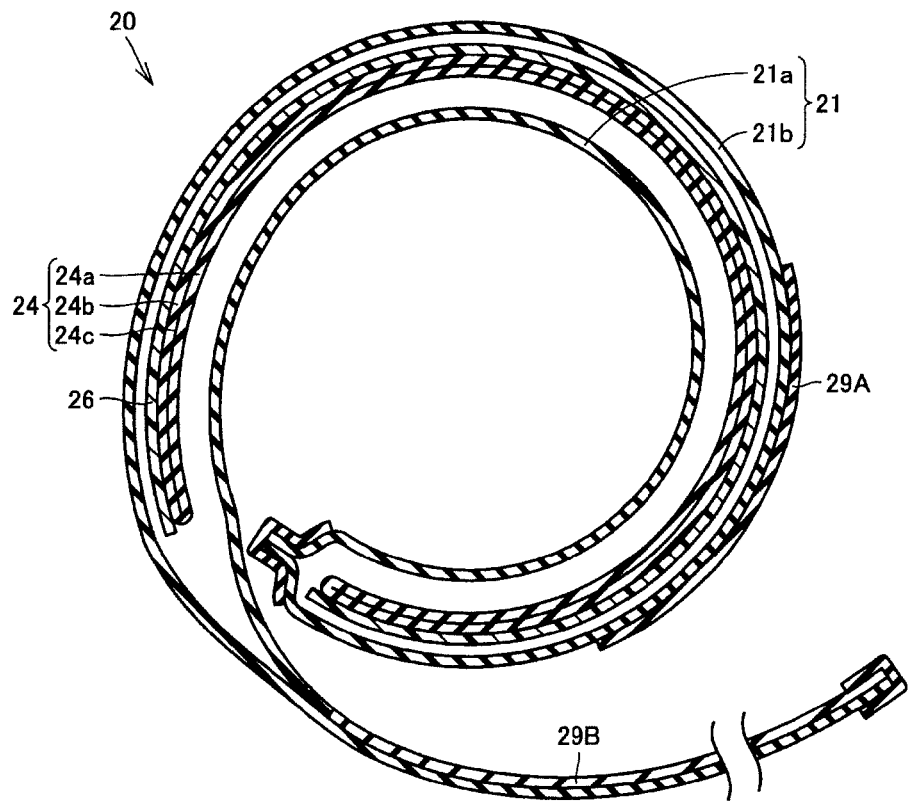
FIG. 3 is a cross-sectional view of the cuff shown in FIG. 1 sectioned along a plane orthogonal to an axial direction.
Figure 4:
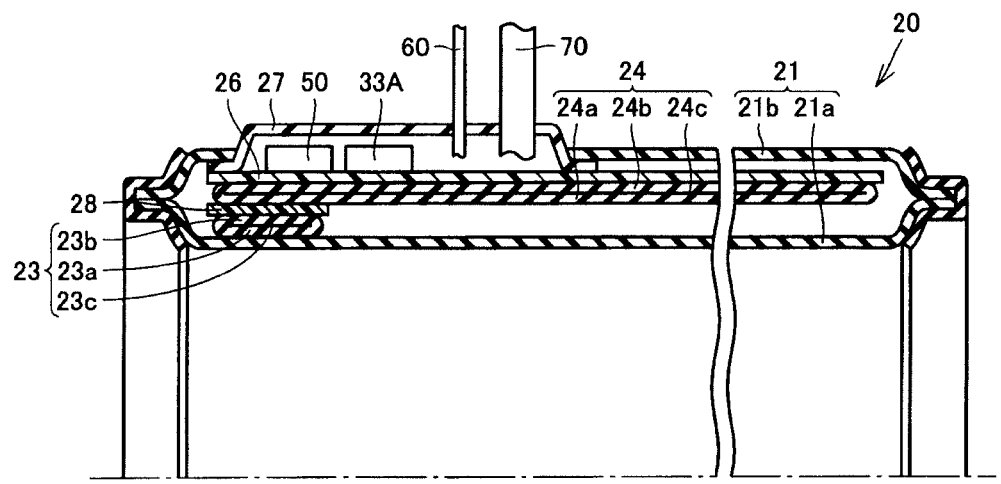
FIG. 4 is a cross-sectional view of the cuff shown in FIG. 1 sectioned along a plane parallel to the axial direction.

FIG. 1 is a perspective view showing an external structure of the blood pressure information measurement device in Embodiment 1 of the present invention, and FIG. 2 is a development view of the cuff shown in FIG. 1 as seen from an outer circumferential surface side. Also, FIG. 3 is a cross-sectional view of the cuff shown in FIG. 1 sectioned along a plane orthogonal to the axial direction, and FIG. 4 is a cross-sectional view of the cuff shown in FIG. 1 sectioned along a plane parallel to the axial direction. Here, the cross-section shown in FIG. 3 is a cross-section of a portion that does not include an air bladder for pulse wave measurement which will be discussed later. First, the configuration of a blood pressure information measurement device 1A in the present embodiment will be described, with reference to these FIGS. 1 to 4.

As shown in FIG. 1, the blood pressure information measurement device 1A in the present embodiment is provided with a main body 10, a cuff 20, a connection cable 60, and a tube 70. The main body 10 has a box-like casing 11, and a display unit 42 and an operating unit 43 are provided on an upper surface thereof. The main body 10 is placed for use on a placement surface such as a table at the time of measurement. The cuff 20 has a belt-like form that can be wrapped around an upper arm serving as a fitting site, and is covered by an outer cover 21 serving as an outer body. The cuff 20 is fitted for use by being wrapped around the upper arm at the time of measurement. Note that the connection cable 60 and the tube 70 each connect the separately constituted main body 10 and cuff 20.

As shown in FIGS. 2 to 4, the cuff 20 is mainly provided with the abovementioned outer cover 21, a small-volume air bladder 23 for pulse wave measurement as a first fluid bag, a large-volume air bladder 24 for blood pressure value measurement as a second fluid bag, a curler 26 as a curved elastic plate, and a cushion material 28 as a vibration damping member.

As shown in FIGS. 1, 3, and 4, the outer cover 21 is a bag-shaped member formed by laying an inside cover 21a that will contact the surface of the upper arm in the fitted state and an outside cover 21b that will be positioned on the outermost side in the fitted state one on top of the other, and joining the peripheral edges thereof (e.g., stitching, welding). The air bladder 23 for pulse wave measurement, the cushion material 28, the air bladder 24 for blood pressure value measurement, and the curler 26 are layered sequentially in the stated order from the inner side and housed in the internal space of the outer cover 21.

As shown in FIGS. 1 to 3, surface fasteners 29A and 29B are provided on the outer circumferential surface of the outer cover 21 near one end in the longitudinal direction and the inner circumferential surface near the other end, respectively. Here, the surface fastener 29A consists of a hook fastener, for example, and the surface fastener 29B consists of a loop fastener, for example. These surface fasteners 29A and 29B are fastened by wrapping the outer cover 21 around the upper arm, and laying the portion near one end of the outer cover 21 and the portion near the other end one on top of the other on the surface of the upper arm. The cuff 20 will thereby be securely fitted on the upper arm. That is, the surface fasteners 29A and 29B are equivalent to fastening portions at the time of fitting the cuff 20 on the upper arm.

As for the inside cover 21a of the outer cover 21, according to one or more embodiments of the present invention, a member that is sufficiently rich in elasticity is used, so that the compression force applied to the upper arm by expansion of the air bladder 23 for pulse wave measurement and the air bladder 24 for blood pressure value measurement is not inhibited by the inside cover 21a. As for the outside cover 21b of the outer cover 21, on the other hand, a member that is lacking in elasticity as compared with the inside cover 21a is used. From such a viewpoint, a fabric or the like consisting of a synthetic fiber such as polyamide (PA) or polyester whose magnitude of elasticity can be adjusted comparatively easily is used for the outer cover 21.

As shown in FIG. 4, according to one or more embodiments of the present invention, the air bladder 23 for pulse wave measurement consists of a bag-shaped member preferably formed using a resin sheet, and has an inner circumferential portion 23a that will be positioned on the inner side in the fitted state, an outer circumferential portion 23b that will be positioned outer side in the fitted state, and an inner cavity 23c defined by the inner circumferential portion 23a and the outer circumferential portion 23b. A bag-shaped member formed by laying two resin sheets, for example, one on top of the other and welding the peripheral edges thereof can be used as the air bladder 23 for pulse wave measurement. The inner cavity 23c of the air bladder 23 for pulse wave measurement is connected to an inflation pump 31B and an exhaust valve 32B (see FIG. 5) which will be discussed later, via a first piping portion L1 and a second piping portion L2 (see FIG. 5) which will be discussed later, and inflation/deflation thereof is performed by the inflation pump 31B and the exhaust valve 32B. Note that in order to achieve the proper compression force to be applied to the upper arm, a member obtained by a gusset being formed on a side portion thereof in the width direction may be used as the air bladder 23 for pulse wave measurement.

As shown in FIGS. 3 and 4, according to one or more embodiments of the present invention, the air bladder 24 for blood pressure value measurement consists of a bag-shaped member preferably formed using a resin sheet, and has an inner circumferential portion 24a that will be positioned on the inner side in the fitted state, an outer circumferential portion 24b that will be positioned outside in the fitted state, and an inner cavity 24c defined by the inner circumferential portion 24a and the outer circumferential portion 24b. A bag-shaped member formed by laying two resin sheets, for example, one on top of the other and welding the peripheral edges thereof can be used as the air bladder 24 for blood pressure value measurement. The inner cavity 24c of the air bladder 24 for blood pressure value measurement is connected to the inflation pump 31B and the exhaust valve 32B (see FIG. 5) discussed later, via the first piping portion L1 (see FIG. 5) discussed later, and inflation/deflation is performed by the inflation pump 31B and the exhaust valve 32B. Note that in order to achieve the proper compression force to be applied to the upper arm, a member obtained by a gusset being formed in a side portion thereof in the width direction may be used as the air bladder 24 for blood pressure value measurement.

Note that, as for the material of the resin sheets constituting the air bladder 23 for pulse wave measurement and the air bladder 24 for blood pressure value measurement, any material that is rich in elasticity and does not leak air from the inner cavity after being welded can be used. From such a viewpoint, according to one or more embodiments of the present invention, an ethylene-vinyl acetate copolymer (EVA), flexible polyvinyl chloride (PVC), polyurethane (PU), polyamide (PA), crude rubber and the like are given as materials for the resin sheet.

As shown in FIGS. 2 and 4, the air bladder 24 for blood pressure value measurement is disposed so as to be positioned across substantially an entirety of the cuff 20 in the width direction. On the other hand, the air bladder 23 for pulse wave measurement is disposed so as to be positioned only on one edge side of the cuff 20 in the width direction. Here, the edge of the cuff 20 in the width direction on the side where the air bladder 23 for pulse wave measurement is disposed is the edge disposed on the proximal side in the fitted state, and thus the air bladder 23 for pulse wave measurement will, in the fitted state, be wrapped only around the proximal side of the upper arm serving as the fitting site. On the other hand, the air bladder 24 for blood pressure value measurement will, in the fitted state, be wrapped across an entirety of the upper arm serving as the fitting site including the proximal side and the distal side. Here, because the air bladder 23 for pulse wave measurement is overlaid with the air bladder 24 for blood pressure value measurement so as to be positioned on the inner side of the air bladder 24 for blood pressure value measurement in the fitted state, the air bladder 24 for blood pressure value measurement will also cover the outer side of the air bladder 23 for pulse wave measurement at the above one edge side of the cuff 20 in the width direction.

According to one or more embodiments of the present invention, the air bladder 23 for pulse wave measurement has a smaller volume than the air bladder 24 for blood pressure value measurement. According to one or more embodiments of the present invention, the air volume of the air bladder 23 for pulse wave measurement is no more than one-fifth of the air volume of the air bladder 24 for blood pressure value measurement. As an example, the size of the air bladder 23 for pulse wave measurement is about 20 mm×200 mm, and the size of the air bladder 24 for blood pressure value measurement is about 90-105 mm×200 mm.

As shown in FIG. 4, the cushion material 28 is disposed between the air bladder 23 for pulse wave measurement and the air bladder 24 for blood pressure value measurement that are disposed one on top of the other. The cushion material 28 is for ensuring that vibrations produced in the air bladder 23 for pulse wave measurement and the air bladder 24 for blood pressure value measurement are not mutually transmitted, and according to one or more embodiments of the present invention, a sponge member such as a urethane sheet is used, for example. This cushion material 28 is the same size as the air bladder 23 for pulse wave measurement or slightly larger than the air bladder 23 for pulse wave measurement.

As shown in FIGS. 3 and 4, the curler 26 consists of a flexible member configured to be elastically deformable in the diameter direction by being wrapped circularly, and has cuts extending in the axial direction in prescribed positions in the circumferential direction. As a result of these cuts, the curler 26 elastically is deformed stretchably in the diameter direction by an external force being applied. That is, although deforming in the diameter direction under the action of an external force, the curler 26 restores to its original state in the case where the external force is removed. The curler 26 is thereby configured so as to follow the contours of the upper arm by maintaining its own annular form. Also, the air bladder 24 for blood pressure value measurement is fixed by being adhered to the inner circumferential surface of the curler 26 via an adhesive member such as double-sided tape which is not illustrated. This curler 26 is to make it easier for the test subject to fit the cuff 20 on the upper arm by himself or herself, and for biasing the air bladder 24 for blood pressure value measurement and the air bladder 23 for pulse wave measurement toward the upper arm side in the state where the cuff 20 is fitted on the upper arm. Note that the curler 26 is formed with a resin member such as polypropylene (PP), for example, so as to exhibit sufficient elastic force.

As shown in FIGS. 1, 2, and 4, a cover 27 is provided at a prescribed position on the outer circumferential surface side of the cuff 20. The cover 27 is constituted by a hard resin member such as ABS resin, for example, and has a box-like form that is open at the bottom. The cover 27 is fitted to a prescribed position of the outer circumferential surface of the abovementioned curler 26, and a housing space is thereby defined by the cover 27 and the portion of the curler 26 facing the cover 27. The ends of the abovementioned connection cable 60 and tube 70 on the cuff 20 side are respectively drawn into this housing space, and a pressure sensor 33A and a 2-port valve 50 which will be discussed later are also housed therein.

Figure 5:
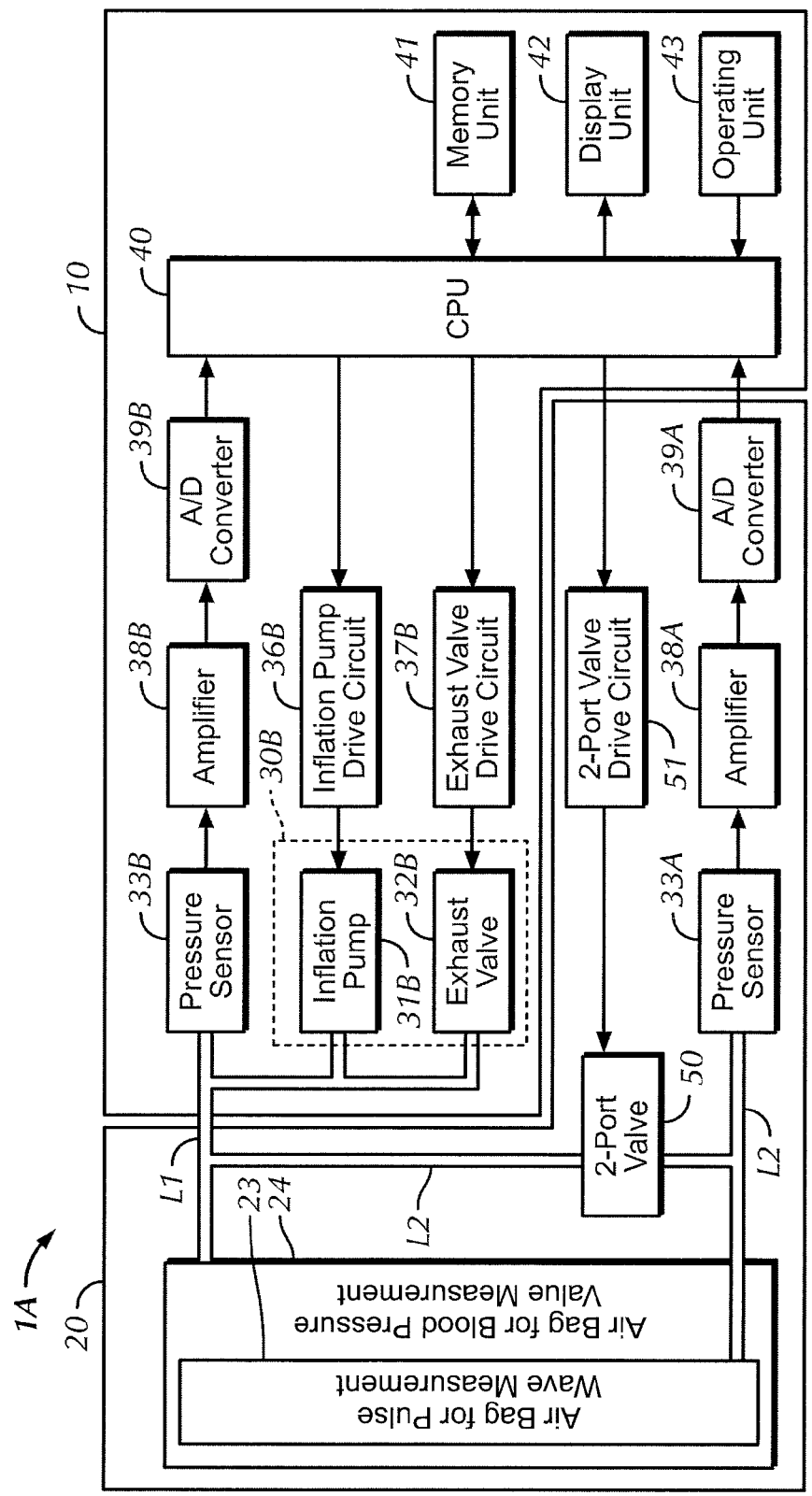
FIG. 5 is a diagram showing a configuration of functional blocks of the blood pressure information measurement device in Embodiment 1 of the present invention.

FIG. 5 is a diagram showing a configuration of functional blocks of the blood pressure information measurement device in the present embodiment. Next, the configuration of the functional blocks of the blood pressure information measurement device 1A in the present embodiment will be described, with reference to this FIG. 5.

As shown in FIG. 5, the blood pressure information measurement device 1A in the present embodiment mainly has, in addition to the abovementioned air bladder 23 for pulse wave measurement, air bladder 24 for blood pressure value measurement, display part 42 and operating unit 43, the pressure sensor 33A as a first pressure detection unit, an inflation pump 31B and an exhaust valve 32B as an inflation/deflation mechanism 30B, a pressure sensor 33B as a second pressure detection unit, a central processing unit (CPU) 40 as a control portion, a memory unit 41 as memory means, a first piping portion L1 and a second piping portion L2 as piping, and the 2-port valve 50 as an opening/closing valve. Of these, the inflation pump 31B, the exhaust valve 32B, the pressure sensor 33B, the CPU 40, the memory unit 41 and a portion of first piping portion L1 are provided in the main body 10, and the pressure sensor 33A, a portion of the first piping portion L1, the second piping portion L2 and the 2-port valve 50 are provided in the cuff 20.

The inflation pump 31B and the exhaust valve 32B serving as the inflation/deflation mechanism 30B are for inflating/deflating the air bladder 23 for pulse wave measurement and the air bladder 24 for blood pressure value measurement. The drive of the inflation pump 31B is controlled by an inflation pump drive circuit 36B that has received a command from the CPU 40, and the inflation pump 31B inflates the air bladder 23 for pulse wave measurement and the air bladder 24 for blood pressure value measurement by introducing compressed air into the air bladder 23 for pulse wave measurement and the air bladder 24 for blood pressure value measurement. The drive of the exhaust valve 32B is controlled by an exhaust valve drive circuit 37B that has received a command from the CPU 40, and the exhaust valve 32B maintains the internal pressure of the air bladder 23 for pulse wave measurement and the air bladder 24 for blood pressure value measurement in a closed state, and deflates the internal pressure of the air bladder 23 for pulse wave measurement and the air bladder 24 for blood pressure value measurement by discharging the air in the air bladder 23 for pulse wave measurement and the air bladder 24 for blood pressure value measurement in an open state. Note that the abovementioned inflation pump drive circuit 36B and exhaust valve drive circuit 37B are also provided in the main body 10, similarly to the inflation pump 31B and the exhaust valve 32B.

The pressure sensor 33A is for detecting the internal pressure of the air bladder 23 for pulse wave measurement. The pressure sensor 33A detects the internal pressure of the air bladder 23 for pulse wave measurement, and outputs a signal that depends on the detected internal pressure to an amplifier 38A. The amplifier 38A amplifies the signal input from the pressure sensor 33A, and outputs a signal after amplification to an analog/digital (A/D) converter 39A. The A/D converter 39A converts the signal after amplification input from the amplifier 38A from an analog signal into a digital signal, and outputs the digital signal after conversion to the CPU 40. Note that the abovementioned amplifier 38A and A/D converter 39A are also provided in the cuff 20, similarly to the pressure sensor 33A.

The pressure sensor 33B is for detecting the internal pressure of the air bladder 24 for blood pressure value measurement. The pressure sensor 33B detects the internal pressure of the air bladder 24 for blood pressure value measurement, and outputs a signal that depends on the detected internal pressure to an amplifier 38B. The amplifier 38B amplifies the signal input from the pressure sensor 33B, and outputs a signal after amplification to an A/D converter 39B. The A/D converter 39B converts the signal after amplification input from the amplifier 38B from an analog signal into a digital signal, and outputs the digital signal after conversion to the CPU 40. Note that the abovementioned amplifier 38B and A/D converter 39B are also provided in the main body 10, similarly to the pressure sensor 33B.

The first piping portion L1 connects the air bladder 24 for blood pressure value measurement, the inflation pump 31B, the exhaust valve 32B and the pressure sensor 33B. A portion of this first piping portion L1 is equivalent to the flexible tube 70 connecting the abovementioned main body 10 and cuff 20.

The second piping portion L2 branches from a prescribed position of the first piping portion L1, and connects the first piping portion L1, the air bladder 23 for pulse wave measurement and the pressure sensor 33A. The air bladder 23 for pulse wave measurement is thereby mainly connected to the inflation pump 31B and the exhaust valve 32B through the first piping portion L1 and the second piping portion L2, and is connected to the pressure sensor 33A through the second piping portion L2.

The 2-port valve 50 is provided at a prescribed position of the second piping portion L2. The drive of the 2-port valve 50 is controlled by a 2-port valve drive circuit 51 that has received a command from the CPU 40, and the 2-port valve 50 allows communication between the first piping portion L1 and the air bladder 23 for pulse wave measurement in an open state, and maintains the internal pressure of the air bladder 23 for pulse wave measurement by preventing communication between the first piping portion L1 and the air bladder 23 for pulse wave measurement in a closed state. Note that the abovementioned 2-port valve drive circuit 51 is provided in the cuff 20, similarly to the 2-port valve 50.

The operating unit 43 is for receiving user operations and outputting received operations to the CPU 40, and is constituted by push buttons or the like, for example. The display unit 42 is for displaying an operating state of the blood pressure information measurement device 1A, information such as the measurement results of blood pressure values and the measurement results of an index indicating the degree of arteriosclerosis that are output from the CPU 40 after measurement, and the like, and is constituted by a liquid crystal display (LCD), for example. The memory unit 41 is for storing programs that are executed by the CPU 40, information such as the above measurement results, and the like, and is constituted by random access memory (RAM) or read only memory (ROM), for example.

The CPU 40 is for controlling the overall operations of the blood pressure information measurement device 1A, and receives input from the operating unit 43 and the memory unit 41, and outputs a variety of information to the display unit 42 and the memory unit 41. Also, the CPU 40 receives input of information on pressure detected with the pressure sensors 33A and 33B, and generates and outputs signals for driving the inflation pump 31B, the exhaust valve 32B and the 2-port valve 50. Furthermore, the CPU 40 functions as a blood pressure value acquisition unit that calculates and acquires blood pressure values based on the pressure information input from the pressure sensor 33B, and also functions as a pulse wave acquisition unit that detects and acquires a pulse wave based on the pressure information input from the pressure sensor 33A, and additionally as an index calculation unit that calculates an index indicating the degree of arteriosclerosis based on the acquired pulse wave.

Description of a specific technique for calculating blood pressure values with the CPU 40 is omitted here, because a known blood pressure value calculation technique such as the oscillometric method is applicable. Also, description of a specific technique for calculating an index indicating the degree of arteriosclerosis with the CPU 40 is omitted here, because known techniques, such as a technique for calculating an index based on the round-trip travel time of the reflected wave (Tr; also expressed as $\Delta Tp$) of an obtained pulse waveform or a technique for calculating an index based on the augmentation index (AI) of an obtained pulse waveform, are applicable.

Note that the connection cable 60 shown in FIG. 1 is equivalent to signal lines connecting the CPU 40 shown in FIG. 5 with the 2-port valve drive circuit 51 and A/D converter 39A that are likewise shown in FIG. 5.

Figure 6:
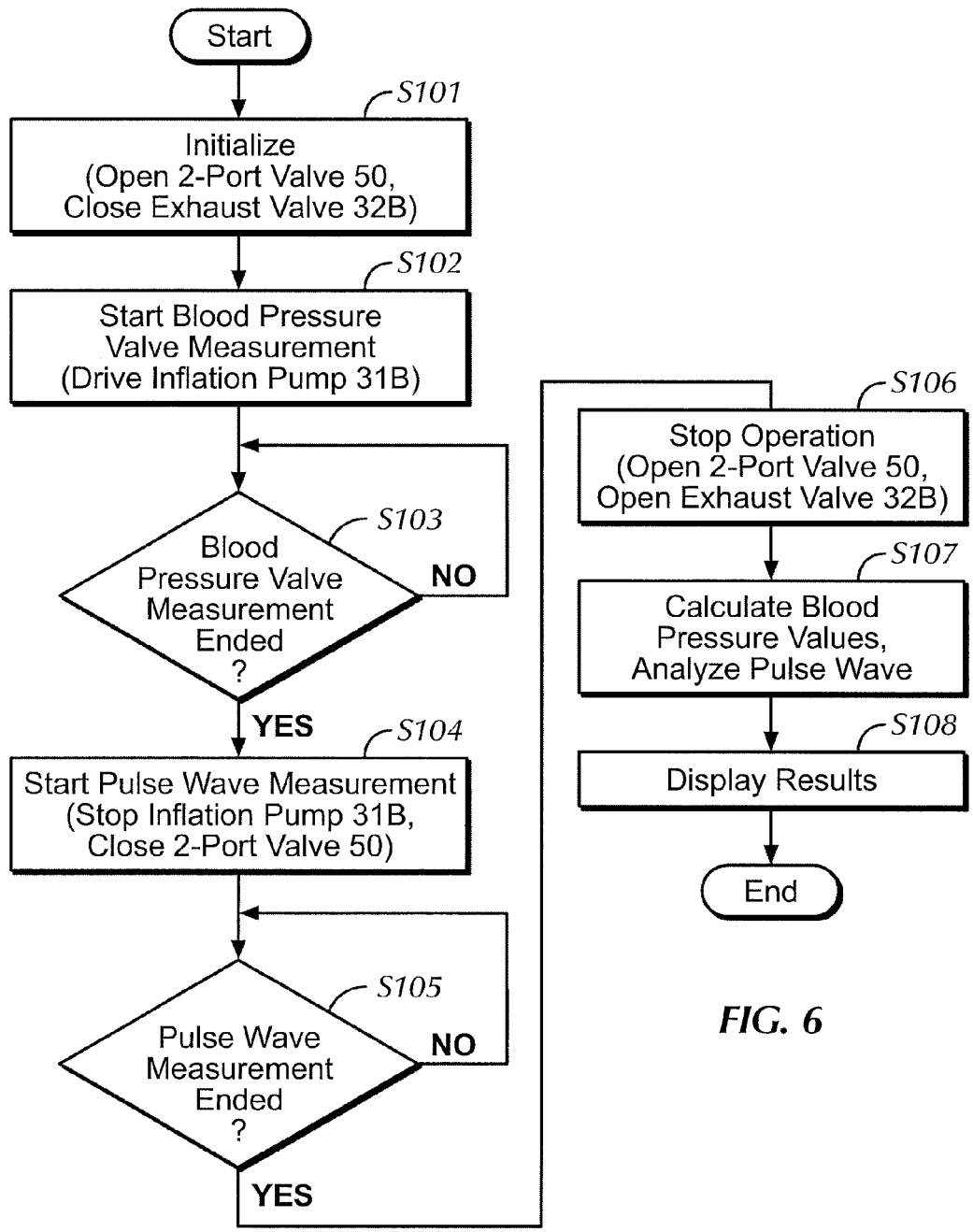
FIG. 6 is a flowchart showing measurement operations of the blood pressure information measurement device in Embodiment 1 of the present invention.
Figure 7:
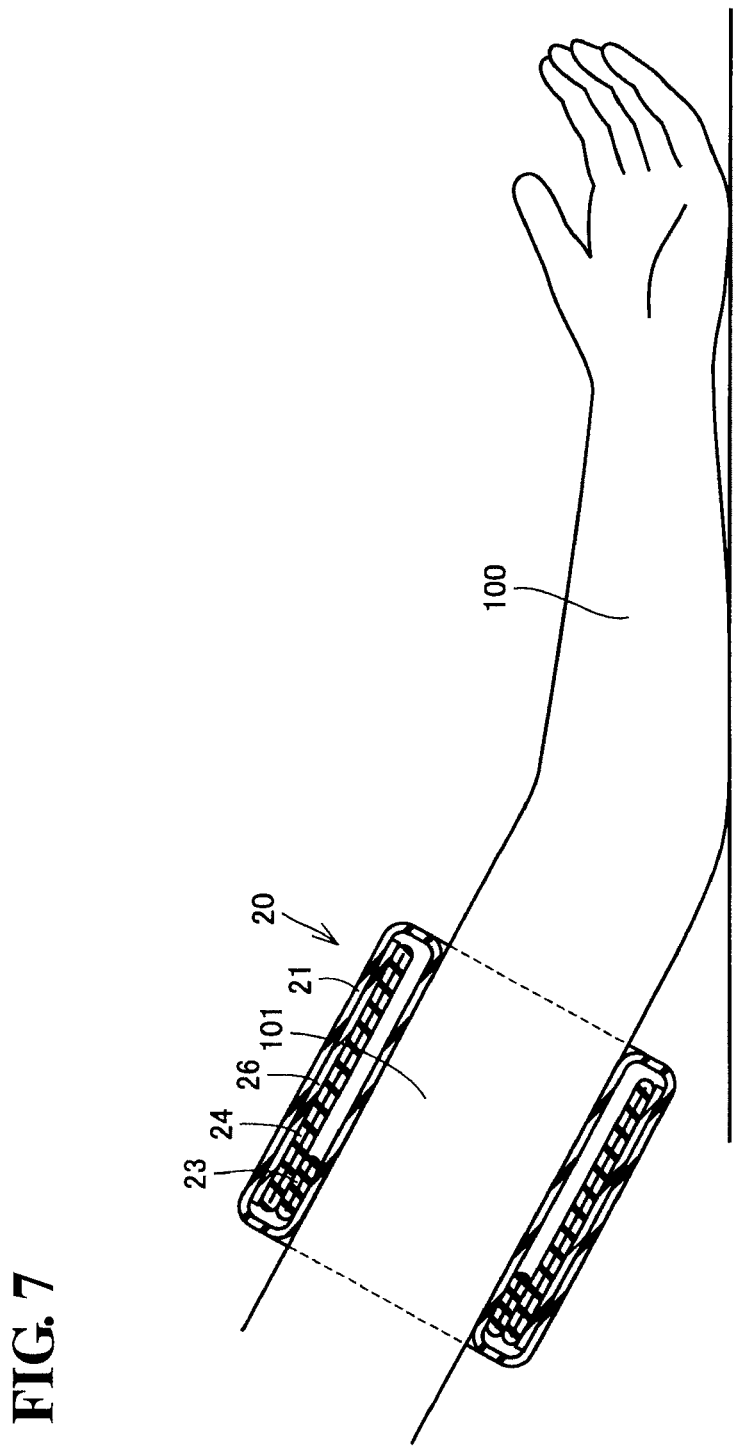
FIG. 7 is a schematic diagram showing a state in which the cuff shown in FIG. 1 is fitted on the upper arm.
Figures 8A, 8B:
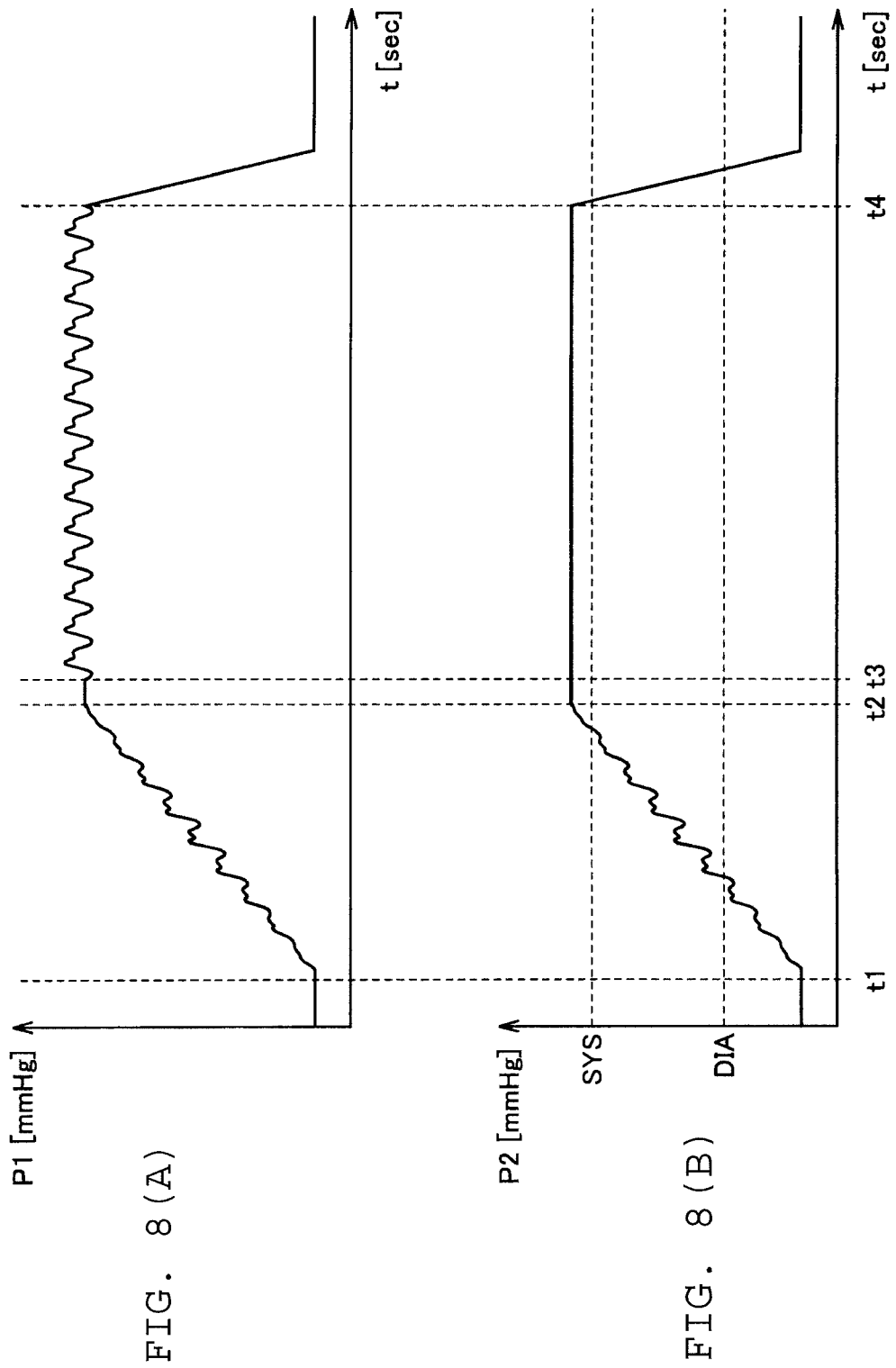
FIGS. 8(A) and 8(B) are graphs showing the change in pressure of an air bladder for pulse wave measurement and an air bladder for blood pressure value measurement during the measurement operations of the blood pressure information measurement device in Embodiment 1 of the present invention.

FIG. 6 is a flowchart showing measurement operations of the blood pressure information measurement device in the present embodiment. A program for executing the measurement operations shown in this flowchart is stored in advance in the memory unit 41 shown in FIG. 5, and the measurement operations shown in the flowchart are realized by the CPU 40 reading out this program from the memory unit 41 and executing the read program. Also, FIG. 7 is a schematic view showing a state in which the cuff shown in FIG. 1 is fitted on the upper arm. Furthermore, FIGS. 8(A) and 8(B) are graphs showing the change in pressure of the air bladder for pulse wave measurement and the air bladder for blood pressure value measurement during the measurement operations of the blood pressure information measurement device in the present embodiment. Here, FIG. 8(A) shows the temporal change in pressure (internal pressure P1) of the inner cavity 23c of the air bladder 23 for pulse wave measurement, and FIG. 8(B) shows the temporal change in pressure (internal pressure P2) of the inner cavity 24c of the air bladder 24 for blood pressure value measurement. Next, the measurement operations of the blood pressure information measurement device 1A in the present embodiment, the change in pressure of the air bladder 23 for pulse wave measurement and the air bladder 24 for blood pressure value measurement during the measurement operations in the state where the cuff 20 is fitted, and the like, will be described, with reference to these FIGS. 6 to 8.

At the time of measuring various blood pressure information using the blood pressure information measurement device 1A in the present embodiment, first, the cuff 20 is fitted on the upper part 101 of the left arm 100 of a test subject, as shown in FIG. 7. At this time, as illustrated, the cuff 20 is fitted so that the air bladder 23 for pulse wave measurement is positioned on the proximal side of the fitting site of the cuff 20. Next, the blood pressure information measurement device 1A starts the measurement operations, as a result of the test subject or the like operating the operating unit 43 of the main body 10.

As shown in FIG. 6, the CPU 40, on receiving a command to start of the measurement operations, initializes the various units (step S101). Specifically, the CPU 40 opens the 2-port valve 50 and closes the exhaust valve 32B.

Next, the CPU 40 starts inflating the air bladder 23 for pulse wave measurement and the air bladder 24 for blood pressure value measurement by driving the inflation pump 31B (step S102). As shown in FIGS. 8(A) and 8(B), the internal pressure P1 of the air bladder 23 for pulse wave measurement and the internal pressure P2 of the air bladder 24 for blood pressure value measurement will thereby respectively start to rise at a time t1 at which the inflation pump 31B is driven. In this inflation process, the CPU 40 acquires pressure information for calculating blood pressure values such as maximum blood pressure (SYS) and minimum blood pressure (DIA). Specifically, the CPU 40 acquires the pressure information based on a pressure signal input from the pressure sensor 33B.

Next, as shown in FIG. 6, the CPU 40 judges whether blood pressure value measurement has ended (step S103), and, if it is judged that blood pressure value measurement has ended (if YES in step S103), starts pulse wave measurement (step S104). Specifically, the CPU 40 stops the drive of the inflation pump 31B, and then closes the 2-port valve 50. As shown in FIGS. 8(A) and 8(B), the internal pressure P1 of the air bladder 23 for pulse wave measurement and the internal pressure P2 of the air bladder 24 for blood pressure value measurement are thereby respectively maintained at a higher pressure than maximum blood pressure at a time t2 at which the drive of the inflation pump 31B is stopped, and the artery will be occluded at the fitting site on the upper arm. Subsequently, from a time t3 at which the 2-port valve 50 is closed, the pulse wave transmitted via subcutaneous tissue from the portion of the artery adjacent to the proximal side end of the occluded artery will be sharply observed in the large-volume air bladder 24 for blood pressure value measurement and the small-volume air bladder 23 for pulse wave measurement that is cut off from the first piping portion L1 and the like connected to the air bladder 24 for blood pressure value measurement. From this time t3, the CPU 40 acquires the pulse wave based on the signal input from the pressure sensor 33A.

Next, as shown in FIG. 6, the CPU 40 judges whether pulse wave measurement has ended (step S105), and, if it is judged that pulse wave measurement has ended (if YES in step S105), transitions to a stop operation (step S106). Specifically, the CPU 40 opens the 2-port valve 50, and also opens the exhaust valve 32B. As shown in FIGS. 8(A) and 8(B), the internal pressure P1 of the air bladder 23 for pulse wave measurement and the internal pressure P2 of the air bladder 24 for blood pressure value measurement thereby respectively start to fall at a time t4 at which the exhaust valve 32B was opened, and return to atmospheric pressure.

Next, as shown in FIG. 6, the CPU 40 performs blood pressure value calculation and pulse wave analysis (step S107). Specifically, the CPU 40 calculates the maximum blood pressure (SYS), the minimum blood pressure (DIA), and an index indicating the degree of arteriosclerosis, based on the acquired pressure information and pulse waves.

Next, the CPU 40 displays the calculated maximum blood pressure, minimum blood pressure, and index indicating the degree of arteriosclerosis on the display unit 42 (step S108). At this time, the CPU 40 may output the measurement results to the memory unit 41 and store the measurement results in the memory unit 41. After the measurement results are displayed, the cuff 20 is removed from the upper arm of the test subject. The series of measurement operations is ended as a result of the above, completing measurement of various types of blood pressure information using the blood pressure information measurement device 1A in the present embodiment.

With the blood pressure information measurement device 1A in the present embodiment described above, the volume of the enclosed space including the inner cavity 23c of the air bladder 23 for pulse wave measurement with which pressure detection is performed by the pressure sensor 33A at the time of pulse wave measurement is configured to be significantly smaller as compared with that in a conventional blood pressure information measurement device, by providing the 2-port valve 50, the portion of the second piping portion L2 connecting the 2-port valve 50 and the air bladder 23 for pulse wave measurement, and the pressure sensor 33A provided on the second piping portion L2 all in the cuff 20. Here, in a conventional blood pressure information measurement device, the abovementioned 2-port valve 50 and pressure sensor 33A are both provided on the main body 10 side.

Thus, with the blood pressure information measurement device 1A in the present embodiment, fluctuations in pressure produced in the air bladder 23 for pulse wave measurement at the time of pulse wave measurement can be extremely sharply observed, enabling the S/N ratio of the pulse wave signal output from the pressure sensor 33A to be raised significantly as compared with that in a conventional blood pressure information measurement device. Accordingly, by adopting the blood pressure information measurement device 1A in the present embodiment, a pulse wave can be measured with high accuracy, and an index indicating the degree of arteriosclerosis can be calculated with maximum accuracy by calculating the index indicating the degree of arteriosclerosis based on the obtained pulse wave.

Here, when the sensitivity of the pulse wave amplitude that can be measured is computed theoretically, in the case where a configuration like the blood pressure information measurement device 1A in the present embodiment is adopted and in the case where a configuration like the conventional blood pressure information measurement device is adopted with reference to the specifications of a typical upper-arm type blood pressure information measurement device, the volume of the enclosed space is about 4100 mm$^3$ for the former and about 7100 mm$^3$ for the latter, and as such, an improvement of approximately 40% will be expected in the case where a configuration like the blood pressure information measurement device 1A in the present embodiment is adopted, as compared with the case where a configuration like the conventional blood pressure information measurement device is adopted. Accordingly, by adopting a configuration like the blood pressure information measurement device 1A in the present embodiment, the S/N ratio will improve by about 67% in general, as compared with the conventional device, which is understood as meaning that a pulse wave can be measured with high accuracy.

Note that with the blood pressure information measurement device 1A in the abovementioned present embodiment, the case was illustrated where the cover 27 is provided on the outer circumferential surface side of the outer cover 21 of the cuff 20, and the 2-port valve 50 and the pressure sensor 33A are disposed inside the cover 27, but as long as the 2-port valve 50 and the pressure sensor 33A are provided in the cuff 20, the disposition position, method of fixing and the like thereof are not particularly restricted.

Also, with the blood pressure information measurement device 1A in the abovementioned present embodiment, the case was illustrated where the connection cable 60 and the tube 70 connecting the main body 10 and the cuff 20 are separate, but it is also naturally possible for them to be integrated.

Figure 9:
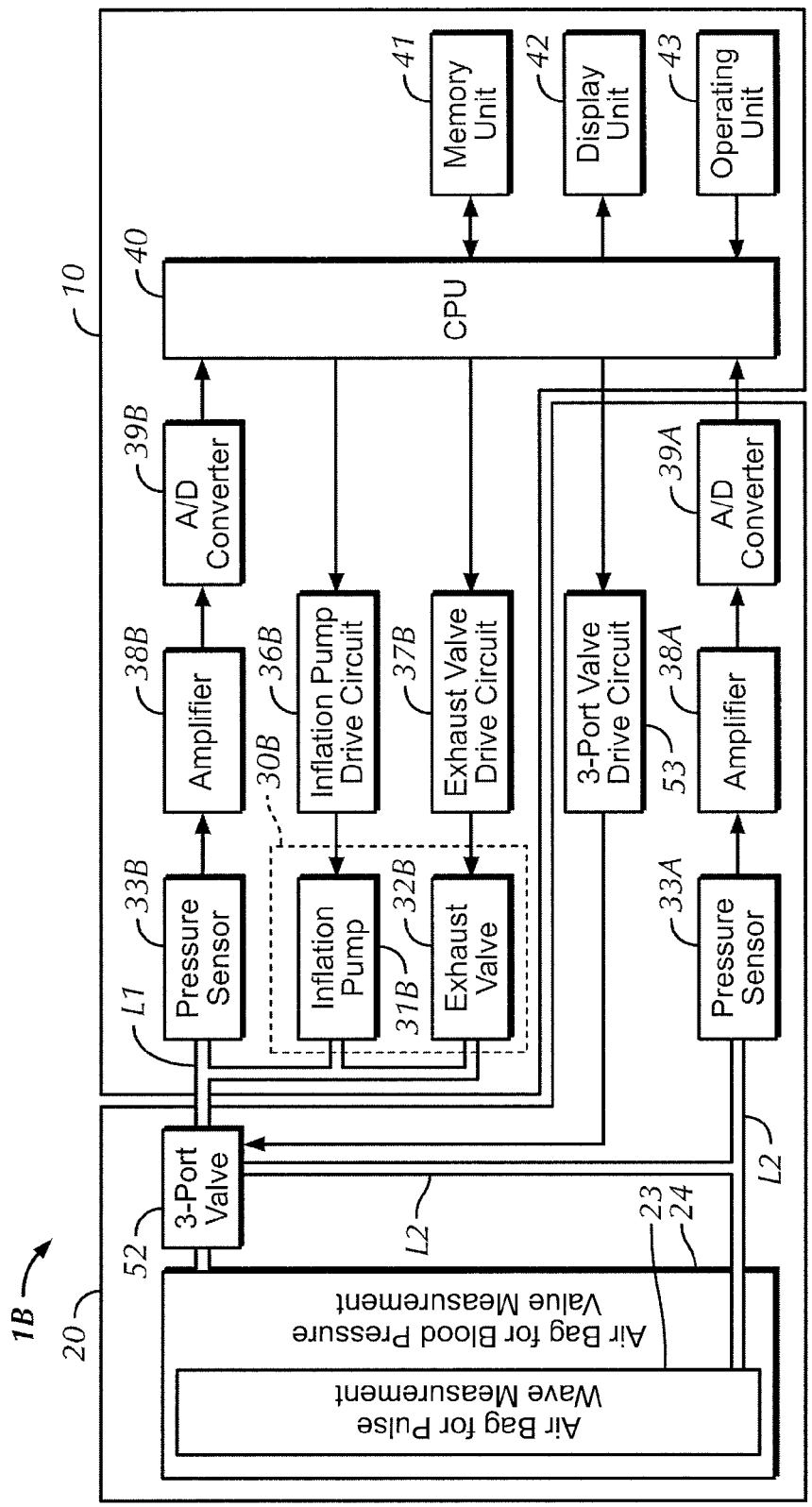
FIG. 9 is a diagram showing a configuration of functional blocks of a blood pressure information measurement device according to a first modification based on Embodiment 1 of the present invention.

FIG. 9 is a diagram showing a configuration of functional blocks of a blood pressure information measurement device according to a first modification based on the present embodiment. Next, a blood pressure information measurement device 1B according to the present modification will be described, with reference to FIG. 9.

As shown in FIG. 9, with the blood pressure information measurement device 1B according to the present modification, the 2-port valve 50 serving as an opening/closing valve provided on the cuff 20 in the blood pressure information measurement device 1A in the abovementioned present embodiment is changed to a 3-port valve 52. In this case, the disposition position of the 3-port valve 52 is the connection point of the first piping portion L1 and the second piping portion L2. The drive of the 3-port valve 52 is controlled by a 3-port valve drive circuit 53 that has received a command from the CPU 40. Note that the fact that the 3-port valve 52 and 3-port valve drive circuit 53 are provided in the cuff 20 is similar to the case of the blood pressure information measurement device 1A in the abovementioned present embodiment.

Here, the 3-port valve 52 may be configured so as to allow communication between the inflation/deflation mechanism 30B and the air bladder 23 for pulse wave measurement in a first state (equivalent to the "open state" in the case of the abovementioned present embodiment) by connecting only the second piping portion L2 and the portion of the first piping portion L1 positioned on the inflation/deflation mechanism 30B side of the position at which the 3-port valve 52 is provided, and to maintain the internal pressure of the air bladder 23 for pulse wave measurement in a second state (equivalent to the "closed state" in the case of the abovementioned present embodiment) by connecting only the portion of the first piping portion L1 on the inflation/deflation mechanism 30B side of the position at which the 3-port valve 52 is provided and the portion of the first piping portion L1 on the air bladder 24 for blood pressure value measurement side of the position at which the 3-port valve 52 is provided to allow communication between the inflation/deflation mechanism 30B and the air bladder 24 for blood pressure value measurement and prevent communication between the first piping portion L1 and the air bladder 23 for pulse wave measurement. In this case, blood pressure measurement is performed after switching the 3-port valve 52 to the second state, and after the end of blood pressure measurement, the 3-port valve 52 is switched to the first state, and the air bladder 23 for pulse wave measurement is inflated using inflation/deflation mechanism 30B, after which the 3-port valve 52 is again switched to the second state to perform pulse wave measurement.

Alternatively, the 3-port valve 52 may be configured so as to allow communication between the air bladder 23 for pulse wave measurement and the air bladder 24 for blood pressure value measurement in a first state (equivalent to the "open state" in the case of the abovementioned present embodiment) by connecting only the second piping portion L2 and the portion of the first piping portion L1 on the air bladder 24 for blood pressure value measurement side of the position at which the 3-port valve 52, and to maintain the internal pressure of the air bladder 23 for pulse wave measurement in a second state (equivalent to the "closed state" in the case of the abovementioned present embodiment) by connecting only the portion of the first piping portion L1 on the inflation/deflation mechanism 30B side of the position at which the 3-port valve 52 is provided and the portion of the first piping portion L1 on the air bladder 24 for blood pressure value measurement side of the position at which the 3-port valve 52 is provided to allow communication between the inflation/deflation mechanism 30B and the air bladder 24 for blood pressure value measurement and prevent communication between the first piping portion L1 and the air bladder 23 for pulse wave measurement. In this case, blood pressure measurement is performed after switching the 3-port valve 52 to the second state, and after the end of blood pressure measurement, the 3-port valve 52 is switched to the first state and inflation of the air bladder 23 for pulse wave measurement is performed by moving air in the air bladder 24 for blood pressure value measurement to the air bladder 23 for pulse wave measurement to achieve pressure equalization, after which the 3-port valve 52 is again switched to the second state to perform pulse wave measurement.

Also in the case where the blood pressure information measurement device 1B according to the present modification described above is adopted, similar effects to the case where the blood pressure information measurement device 1A in the abovementioned present embodiment is adopted can be acquired.

Figure 10:
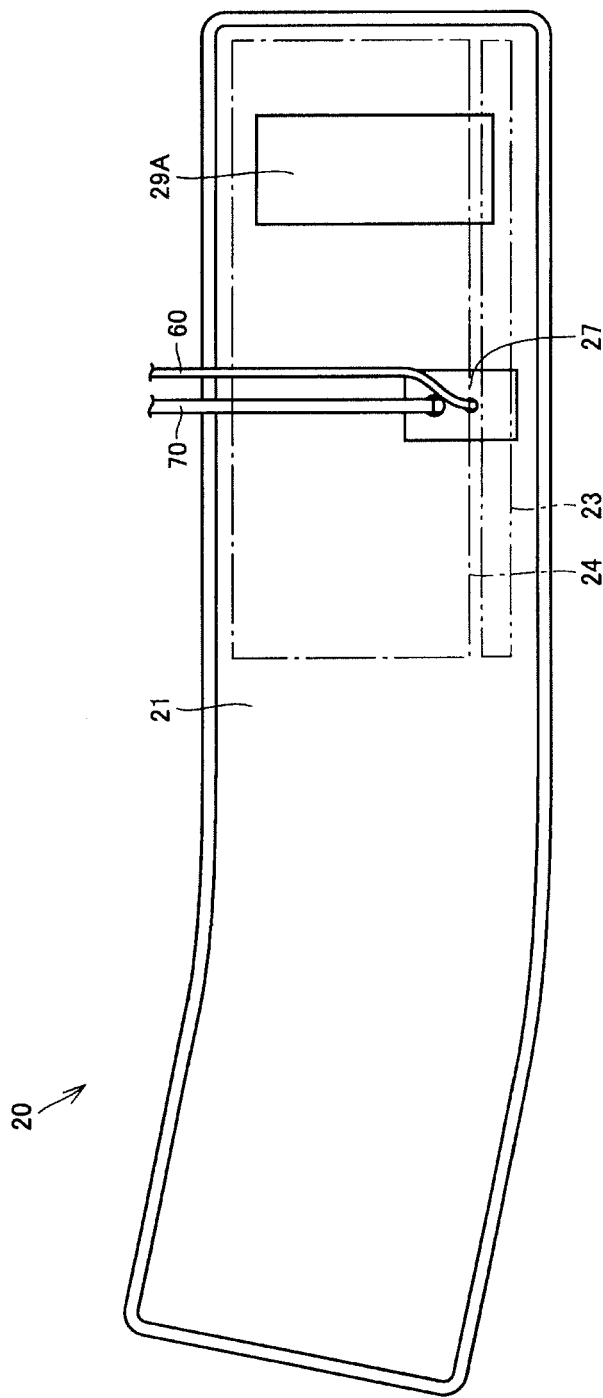
FIG. 10 is a development view of a cuff of a blood pressure information measurement device according to a second modification based on Embodiment 1 of the present invention as seen from an outer circumferential surface side.

FIG. 10 is a development view of the cuff of the blood pressure information measurement device according to a second modification based on Embodiment 1 of the present invention as seen from the outer circumferential surface side. Next, the blood pressure information measurement device according to the present modification will be described, with reference to FIG. 10.

As shown in FIG. 10, with the blood pressure information measurement device according to the present modification, the disposition positions of the air bladder 23 for pulse wave measurement and the air bladder 24 for blood pressure value measurement contained in the cuff 20 differ from those of the blood pressure information measurement device 1A in the abovementioned present embodiment. Specifically, with the blood pressure information measurement device according to the present modification, the air bladder 23 for pulse wave measurement is disposed so as to be positioned only on one edge side of the cuff 20 in the width direction, and the air bladder 24 for blood pressure value measurement is disposed so as to be positioned only on the other edge side of the cuff 20 in the width direction. That is, the air bladder 23 for pulse wave measurement and the air bladder 24 for blood pressure value measurement are disposed alongside each other in the width direction of the cuff 20 (equivalent to the axial direction in the fitted state).

Here, the edge of the cuff 20 in the width direction on the side where the air bladder 23 for pulse wave measurement is disposed is the edge that is disposed on the proximal side in the fitted state, thus the air bladder 23 for pulse wave measurement will be wrapped only around the proximal side of the upper arm serving as the fitting site in the fitted state. On the other hand, the other edge of the cuff 20 in the width direction on the side where the air bladder 24 for blood pressure value measurement is disposed is the edge that is disposed on the distal side in the fitted state, and thus the air bladder 24 for blood pressure value measurement will be wrapped only around the distal side of the upper arm serving as the fitting site in the fitted state.

With the blood pressure information measurement device according to the present modification, not only the air bladder 24 for blood pressure value measurement but also the air bladder 23 for pulse wave measurement is fixedly adhered to the curler 26 that will be positioned on the outer side thereof in the fitted state. Note that with the blood pressure information measurement device according to the present modification, the cushion material 28 serving as a vibration damping member installed in the blood pressure information measurement device 1A in the abovementioned present embodiment is unnecessary.

Similar effects to the case where the blood pressure information measurement device 1A in the abovementioned present embodiment is adopted can also be obtained in the case where the blood pressure information measurement device according to the above-described present modification is adopted.

Embodiment 2

Figure 11:
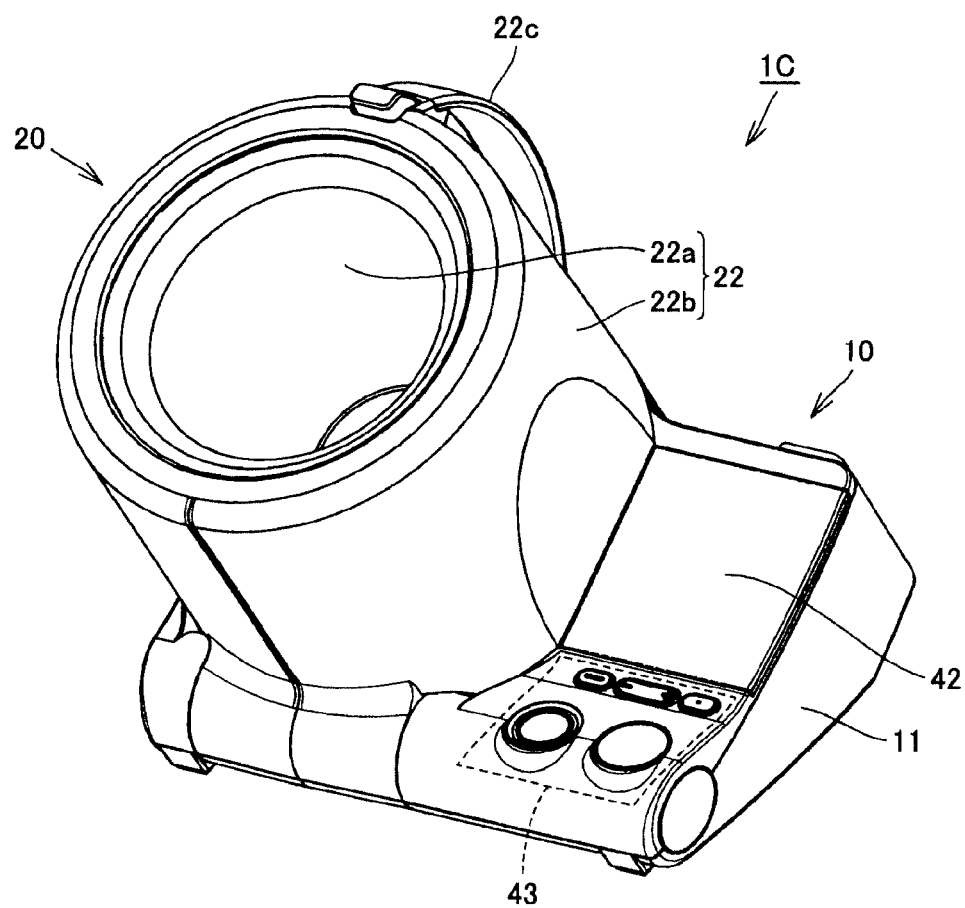
FIG. 11 is a perspective view showing an external structure of a blood pressure information measurement device in Embodiment 2 of the present invention.
Figure 12:
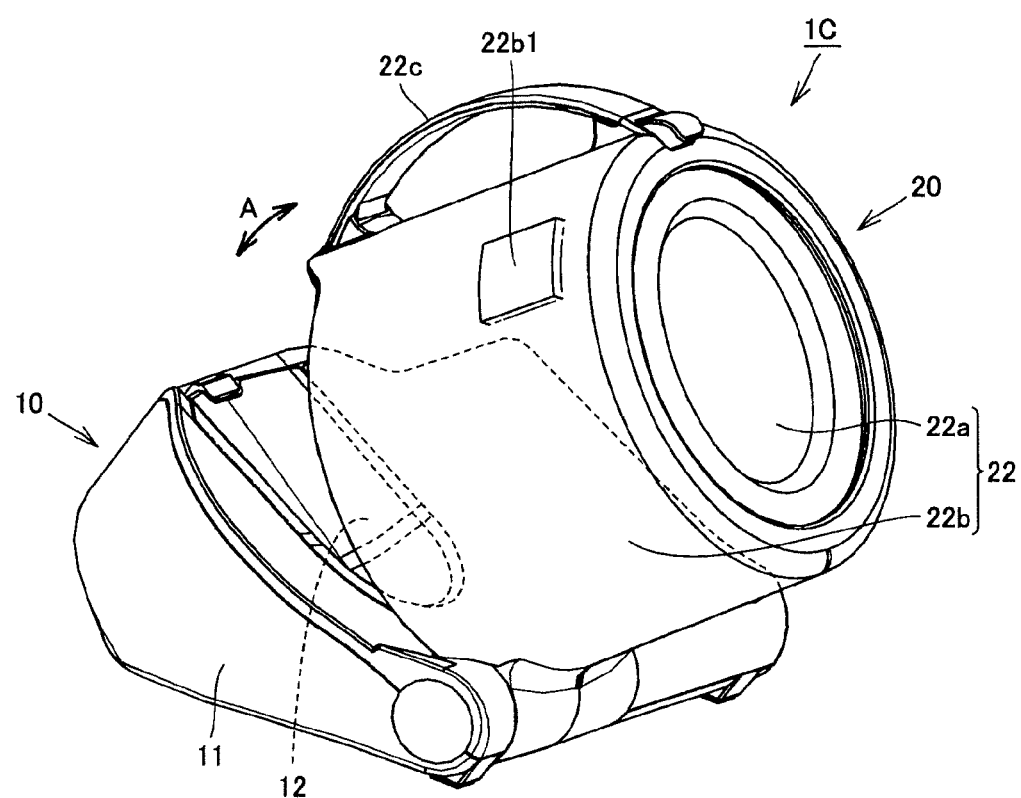
FIG. 12 is a perspective view showing an external structure of the blood pressure information measurement device in Embodiment 2 of the present invention.
Figure 13:
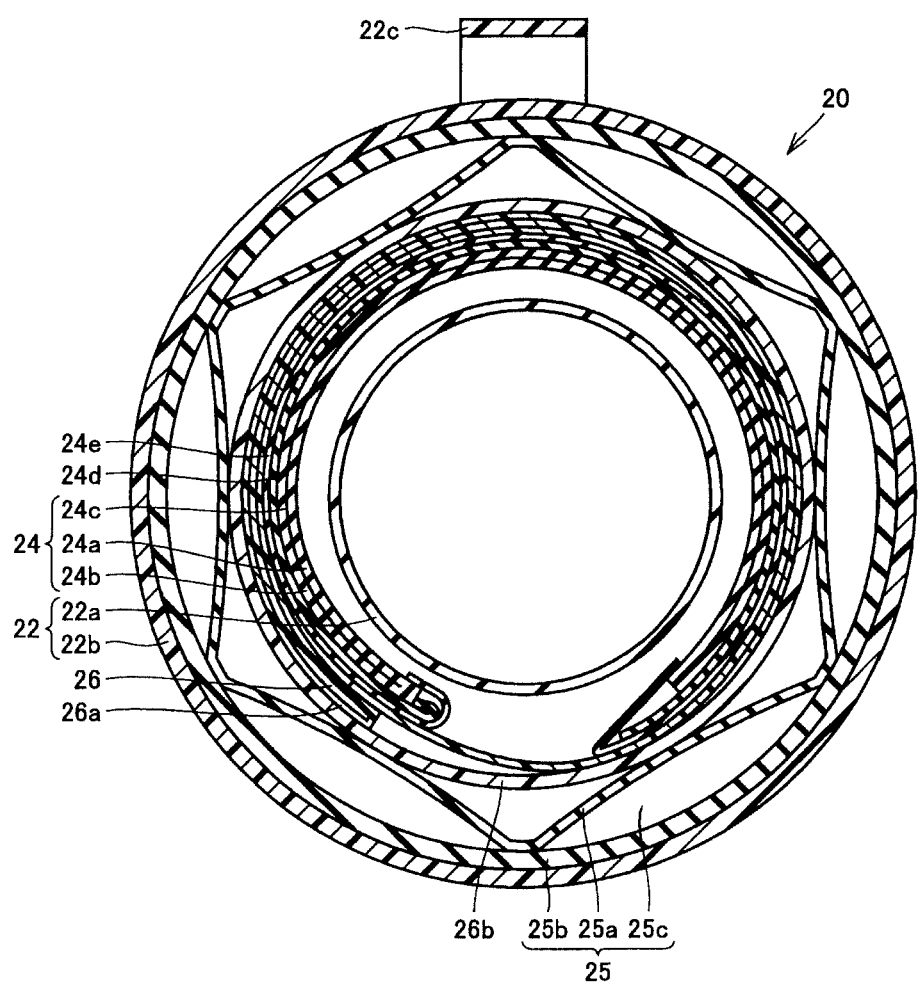
FIG. 13 is a cross-sectional view of the cuff shown in FIGS. 11 and 12 sectioned along a plane orthogonal to the axial direction.
Figure 14:
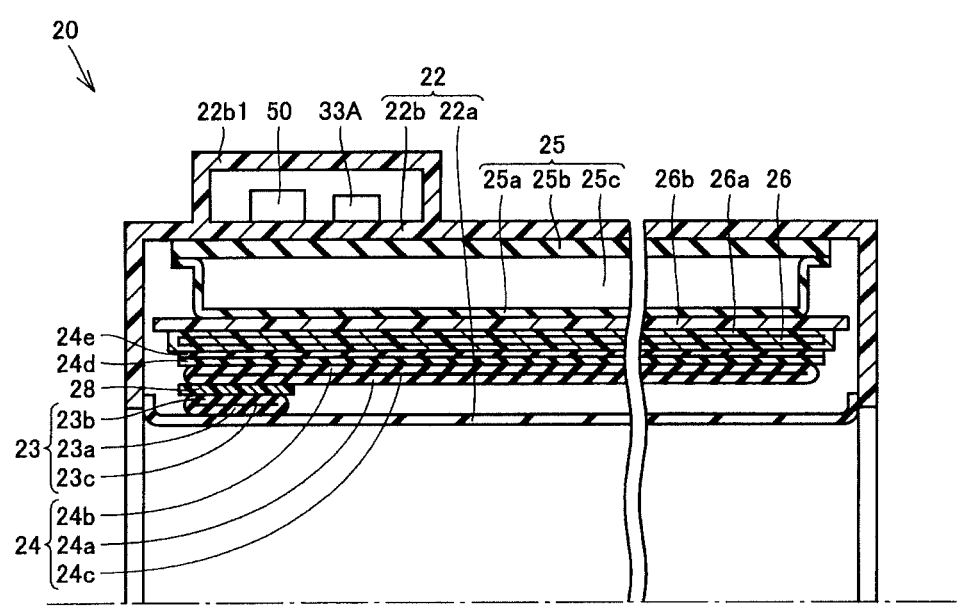
FIG. 14 is a cross-sectional view of the cuff shown in FIGS. 11 and 12 sectioned along a plane parallel to the axial direction.

FIGS. 11 and 12 are perspective views showing an external structure of the blood pressure information measurement device in Embodiment 2 of the present invention. Also, FIG. 13 is a cross-sectional view of the cuff shown in FIGS. 11 and 12 sectioned along a plane orthogonal to the axial direction, and FIG. 14 is a cross-sectional view of the cuff shown in FIGS. 11 and 12 sectioned along a plane parallel to the axial direction. Here, the cross-section shown in FIG. 13 is a cross-section of a portion that does not include the air bladder for pulse wave measurement which will be discussed later. First, the configuration of a blood pressure information measurement device 1C in the present embodiment will be described, with reference to these FIGS. 11 to 14.

As shown in FIGS. 11 and 12, the blood pressure information measurement device 1C in the present embodiment is provided with a main body 10 and a cuff 20. The main body 10 has a box-like casing 11, and a display unit 42 and an operating unit 43 are provided on the upper surface thereof. Also, an elbow rest 12 for placing an elbow at the time of a test subject taking a measurement posture is provided on the upper surface of a portion of the main body 10 adjacent to the display unit 42 and the operating unit 43. This elbow rest 12 is constituted by providing a recessed portion in the upper surface of the casing 11, for example. The main body 10 is placed for use on a placement surface such as a table at the time of measurement. The cuff 20 has an annular form into which an upper arm serving as a fitting site can be inserted, and is covered with an outer cover 22 serving as an outer body. The cuff 20 is coupled to the main body 10 by a hinge or the like so as to be rotatable in the direction of an arrow A shown in FIG. 12, and is fitted for use on the upper arm by the upper arm being inserted at the time of measurement. Note that a handle 22c for facilitating the rotation operation of the cuff 20 coupled to the main body 10 is provided at a prescribed position of the outer circumferential surface of the cuff 20.

As shown in FIGS. 13 and 14, the cuff 20 is mainly provided with the abovementioned outer cover 22, a small-volume air bladder 23 for pulse wave measurement as a first fluid bag, a large-volume air bladder 24 for blood pressure value measurement as a second fluid bag, an even larger volume air bladder 25 for cuff wrapping as a third fluid bag, a curler 26 as a curved elastic board, and a cushion material 28 as a vibration damping member.

As shown in FIGS. 11 to 14, the outer cover 22 includes an inside cover 22a that will contact the surface of the upper arm in the fitted state and an outside shell 22b that will be positioned on the outermost side in the fitted state, and is configured so as to have an approximately cylindrical internal space as a result of the peripheral edge of the inside cover being fixed to the peripheral edge of the outside shell 22b. The internal space of this outer cover 22 mainly houses the air bladder 23 for pulse wave measurement, the cushion material 28, the air bladder 24 for blood pressure value measurement, the curler 26 and the air bladder 25 for cuff wrapping, which are layered sequentially in the stated order from the inner side.

As for the inside cover 22a of the outer cover 22, according to one or more embodiments of the present invention, the member that is sufficiently rich in elasticity is used, so that the compression force applied to the upper arm by expansion of the air bladder 23 for pulse wave measurement, the air bladder 24 for blood pressure value measurement, and the air bladder 25 for cuff wrapping is not inhibited by the inside cover 21a. From such a viewpoint, a fabric or the like consisting of a synthetic fiber such as polyamide (PA) or polyester is used for the inside cover 22a. On the other hand, the outside shell 22b of the outer cover 22 is constituted by a hard resin member such as ABS resin, for example.

As shown in FIGS. 13 and 14, the shape, disposition position and the like of the air bladder 23 for pulse wave measurement, the air bladder 24 for blood pressure value measurement, and the cushion material 28 are similar to the blood pressure information measurement device 1A in the abovementioned Embodiment 1 of the present invention.

On the outer side of the air bladder 24 for blood pressure value measurement, a resin plate 24d and a fabric 24e are disposed sequentially from the inner side. The resin plate 24d has a comparatively high rigidity, and is a shape maintenance member for maintaining the shape of the air bladder 24 for blood pressure value measurement which lacks rigidity. The fabric 24e is a member for reducing slide friction between the resin plate 24d and the curler 26.

The curler 26 consists of a flexible member configured so at to be elastically deformable in the diameter direction by being wrapped circularly, and has cuts extending in the axial direction at prescribed positions in the circumferential direction. As a result of these cuts, the curler 26 elastically is deformed stretchably in the diameter direction by an external force being applied. That is, although deforming in the diameter direction under the action of an external force, the curler 26 restores to its original state in the case where the external force is removed. The curler 26 is thereby configured so as to follow the contours of the upper arm by maintaining its own annular form. This curler 26 is for biasing the air bladder 24 for blood pressure value measurement and the air bladder 23 for pulse wave measurement toward the upper arm side in the state where the cuff 20 is fitted on the upper arm. Note that the curler 26 is formed with a resin member such as polypropylene (PP), for example, so as to exhibit sufficient elastic force. Also, both ends in the circumferential direction of the curler 26 are formed so as to partially overlap when not under the action of an external force. The cuff 20 is thereby configured so that deflation thereof is not inhibited due to both ends of the curler 26 hitting against each other at the time of deflation.

A large portion of the curler 26 is covered with a cloth bag 26a, which is a low-friction bag-shaped member. This cloth bag 26a is a member for reducing slide friction of the curler 26 with the air bladder 25 for cuff wrapping and the resin plate 24d. Also, fabric 26b, which is a low friction member, is disposed over the entire circumference of the outer side of the curler 26. This fabric 26b is a member for reducing slide friction of the curler 26 with the air bladder 25 for cuff wrapping.

According to one or more embodiments of the present invention, the air bladder 25 for cuff wrapping consists of a bag-shaped member formed using a resin sheet, and has an inner circumferential portion 25a positioned on the curler 26 side, an outer circumferential portion 25b positioned in the outside shell 22b side, and an inner cavity 25c defined by the inner circumferential portion 25a and the outer circumferential portion 25b. This inner cavity 25c of the air bladder 25 for cuff wrapping is connected to an inflation pump 31C and an exhaust valve 32C (see FIG. 15) which will be discussed later via a third piping portion L3 (see FIG. 15) which will be discussed later, and inflation/deflation thereof is performed by the inflation pump 31C and the exhaust valve 32C. Note that although inner cavity 25c of the air bladder 25 for cuff wrapping is divided by being partitioned into six equal spaces in the circumferential direction, these spaces communicate with each other, and are uniformly inflated/deflated at the same time by the abovementioned inflation pump 31C and exhaust valve 32C.

As shown in FIGS. 12 and 14, a cover portion 22b1 is provided at a prescribed position on outer circumferential surface side of the cuff 20. The cover portion 22b1 is provided integrally with the outside shell 22b, and housing space is formed therein. This housing space houses a pressure sensor 33A and a 2-port valve 50 which will be discussed later.

Figure 15:
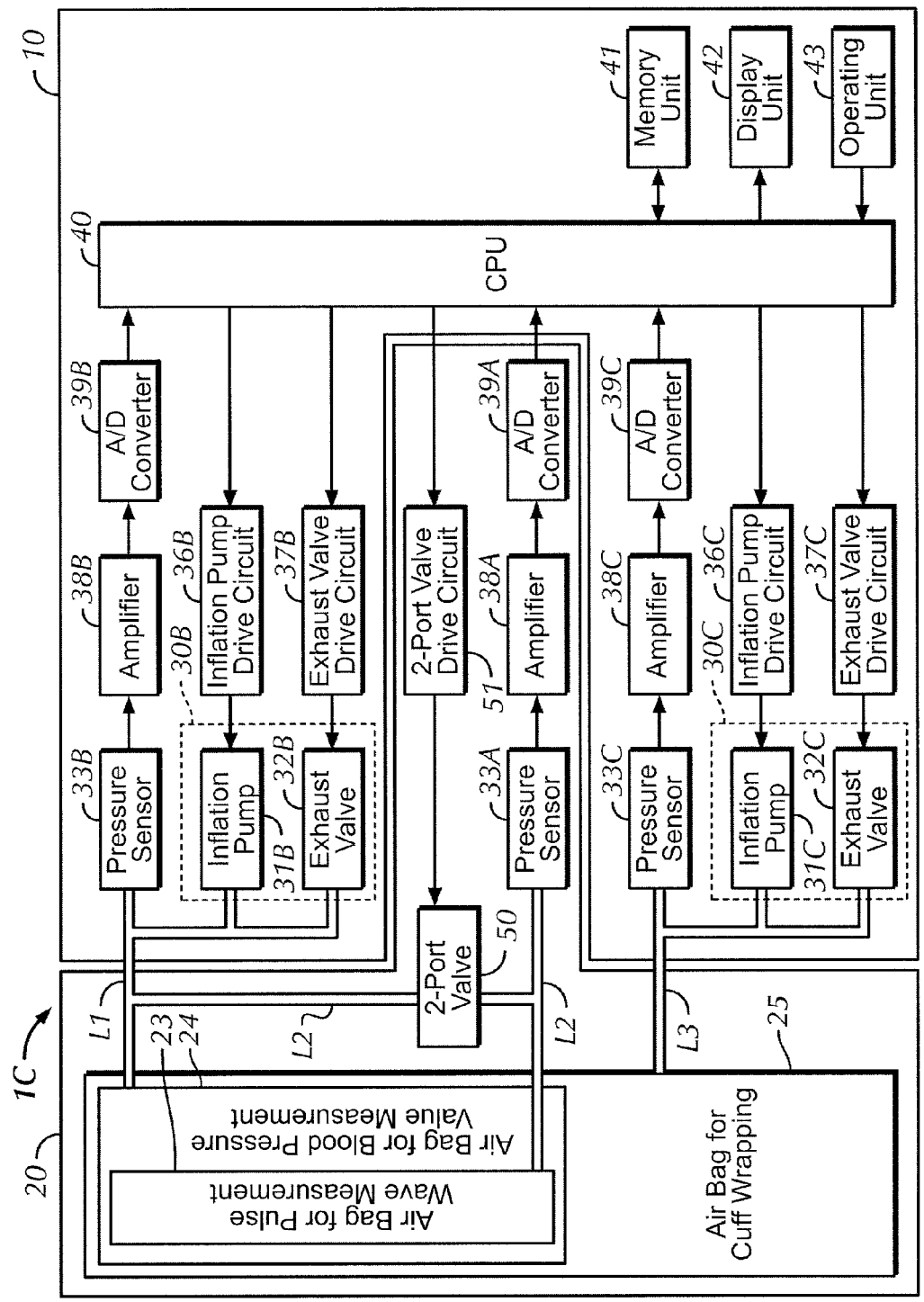
FIG. 15 is a diagram showing a configuration of functional blocks of the blood pressure information measurement device in Embodiment 2 of the present invention.

FIG. 15 is a diagram showing a configuration of functional blocks of the blood pressure information measurement device in the present embodiment. Next, the configuration of the functional blocks of the blood pressure information measurement device 1C in the present embodiment will be described, with reference to this FIG. 15.

As shown in FIG. 15, the blood pressure information measurement device 1C in the present embodiment, mainly has, in addition to the abovementioned air bladder 23 for pulse wave measurement, air bladder 24 for blood pressure value measurement, air bladder 25 for cuff wrapping, display unit 42 and operating unit 43, the pressure sensor 33A as a first pressure detection unit, an inflation pump 31B and an exhaust valve 32B as an inflation/deflation mechanism 30B, a pressure sensor 33B as a second pressure detection unit, an inflation pump 31C and an exhaust valve 32C as an additional inflation/deflation mechanism 30C, a pressure sensor 33C as a third pressure detection unit, a CPU 40 as a control unit, a memory unit 41 as memory means, a first piping portion L1, a second piping portion L2 and a third piping portion L3 as piping, and the 2-port valve 50 as an opening/closing valve. Of these, the inflation pump 31B, the exhaust valve 32B, the pressure sensor 33B, the inflation pump 31C, the exhaust valve 32C, the pressure sensor 33C, the CPU 40, the memory unit 41, a portion of first piping portion L1, and a portion of third piping portion L3 are provided in the main body 10, and the pressure sensor 33A, a portion of the first piping portion L1, the second piping portion L2, a portion of the third piping portion L3, and the 2-port valve 50 are provided in the cuff 20.

The inflation pump 31C and the exhaust valve 32C serving as the additional inflation/deflation mechanism 30C are for inflating/deflating the air bladder 25 for cuff wrapping. The drive of the inflation pump 31C is controlled by an inflation pump drive circuit 36C that has received a command from the CPU 40, and the inflation pump 31C inflates the air bladder 25 for cuff wrapping by introducing compressed air into the air bladder 25 for cuff wrapping. The drive of the exhaust valve 32C is controlled by an exhaust valve drive circuit 37C that has received a command from the CPU 40, and the exhaust valve 32C maintains the internal pressure of the air bladder 25 for cuff wrapping in a closed state and deflates the air bladder 25 for cuff wrapping by discharging the air in the air bladder 25 for cuff wrapping in an open state. Note that the abovementioned inflation pump drive circuit 36C and exhaust valve drive circuit 37C are provided in the main body 10, similarly to the inflation pump 31C and the exhaust valve 32C.

The pressure sensor 33C is for detecting the internal pressure of the air bladder 25 for cuff wrapping. The pressure sensor 33C detects the internal pressure of the air bladder 25 for cuff wrapping, and outputs a signal that depends on the detected pressure to the amplifier 38C. The amplifier 38C amplifies the signal input from the pressure sensor 33C, and outputs a signal after amplification to an A/D 39C. The A/D 39C converts the signal after amplification input from the amplifier 38C from an analog signal into a digital signal, and outputs the digital signal after conversion to the CPU 40. Note that the abovementioned amplifier 38C and A/D 39C are provided in the main body 10, similarly to the pressure sensor 33C.

The third piping portion L3 connects the air bladder 25 for cuff wrapping with the inflation pump 31C, the exhaust valve 32C and the pressure sensor 33C.

Also, the CPU 40, in addition to the functions in the abovementioned Embodiment 1 of the present invention, receives input of information on pressure detected with the pressure sensor 33C, and generates and outputs signals for driving the inflation pump 31C and the exhaust valve 32C.

Figure 16:
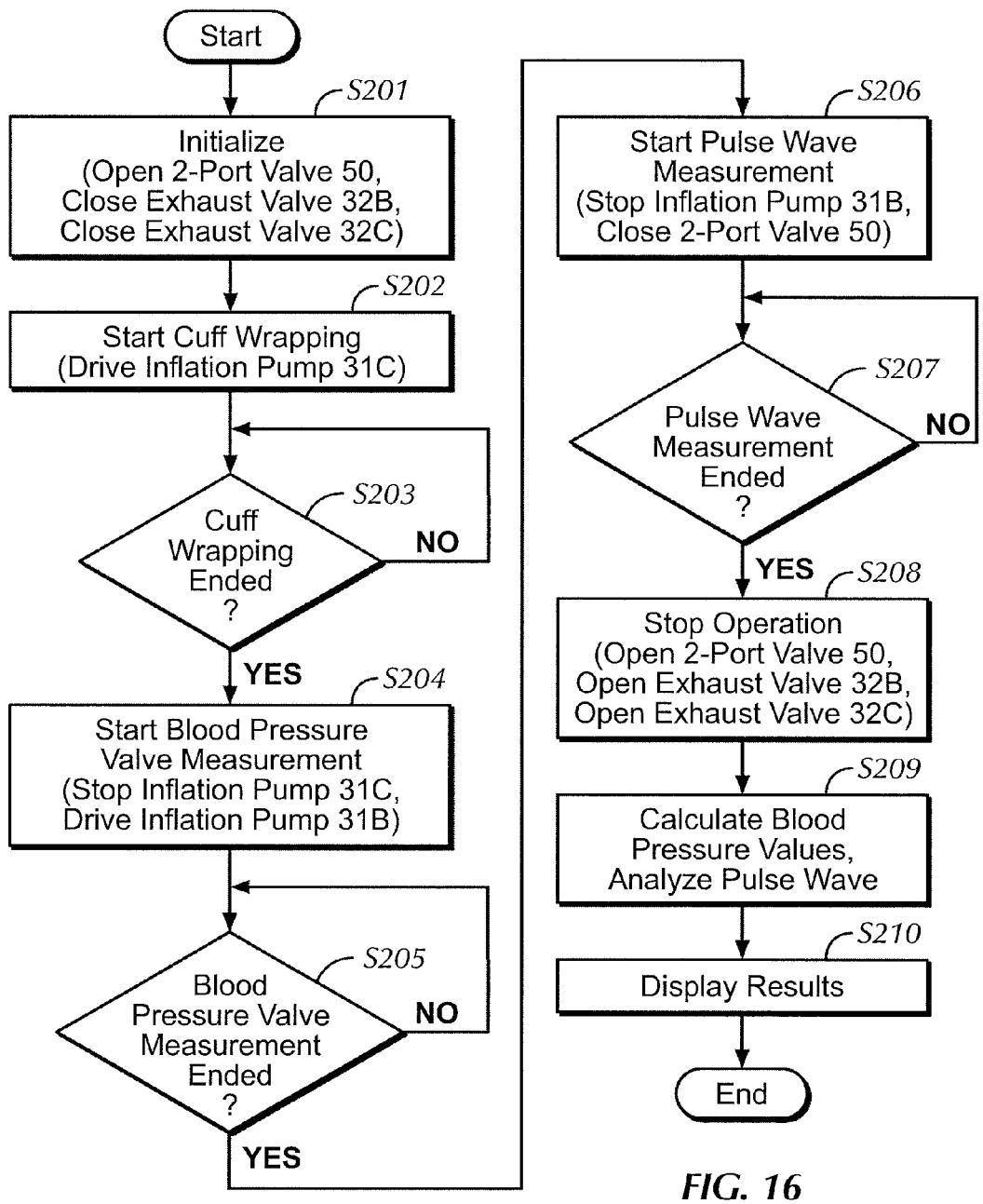
FIG. 16 is a flowchart showing measurement operations of the blood pressure information measurement device in Embodiment 2 of the present invention.
Figure 17:
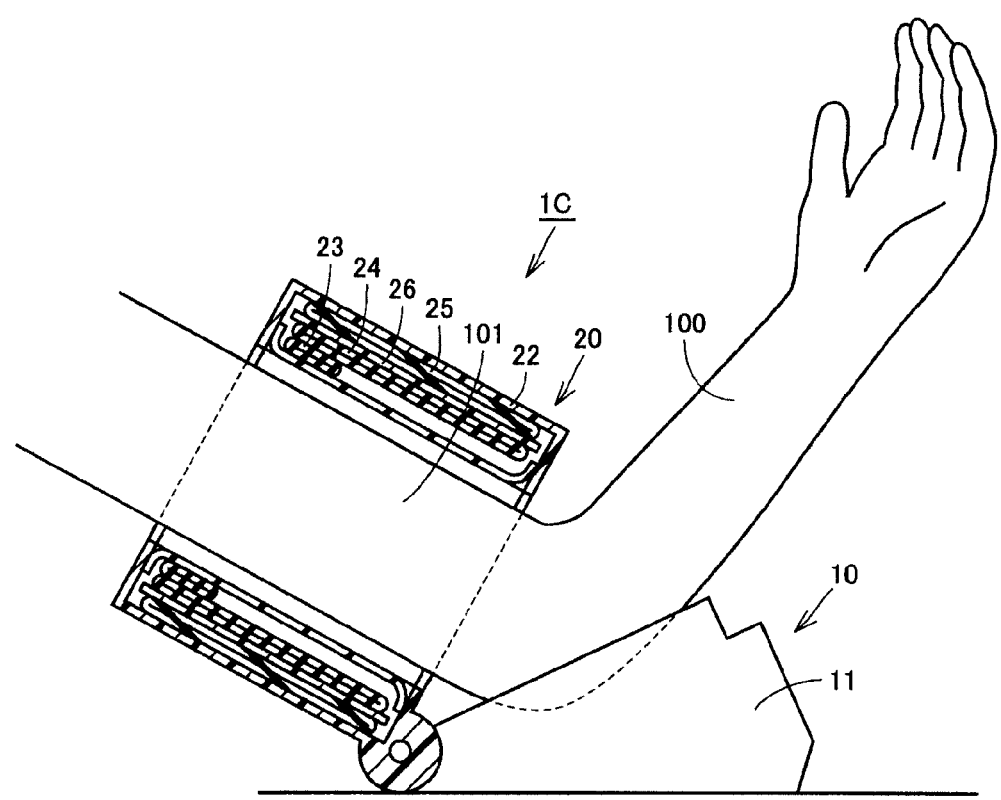
FIG. 17 is a schematic diagram showing a state in which the cuff shown in FIGS. 11 and 12 is fitted on the upper arm.

FIG. 16 is a flowchart showing measurement operations of the blood pressure information measurement device in the present embodiment. A program for executing the measurement operations shown in this flowchart is stored in advance in the memory unit 41 shown in FIG. 15, and the measurement operations shown in the flowchart are realized by the CPU 40 reading out this program from the memory unit 41 and executing the read program. Also, FIG. 17 is a schematic view showing a state in which the cuff shown in FIGS. 11 and 12 is fitted on the upper arm. Next, the measurement operations of the blood pressure information measurement device 1C in the present embodiment, the fitted state of the cuff 20, and the like, will be described, with reference to these FIGS. 16 and 17. Note that because the changes in pressure of the air bladder 23 for pulse wave measurement and the air bladder 24 for blood pressure value measurement during the measurement operations of the blood pressure information measurement device 1C in the present embodiment are similar to those of the blood pressure information measurement device 1A in the abovementioned Embodiment 1 of the present invention, illustration thereof is omitted.

When measuring various blood pressure information using the blood pressure information measurement device 1C in the present embodiment, first, as shown in FIG. 17, the cuff 20 positioned on the main body 10 is tilted forward, the test subject's left arm 100 is inserted into a hollow portion provided in the cuff 20, and an upper arm 101 is positioned in the hollow portion of the cuff 20 by placing the elbow of the inserted left arm 100 on the elbow rest 12 provided in the main body 10. At this time, as illustrated, the air bladder 23 for pulse wave measurement will be positioned in correspondence with the proximal side of the upper arm 101. Next, as a result of the test subject or the like operating the operating unit 43 of the main body 10, the blood pressure information measurement device 1C starts the measurement operations.

As shown in FIG. 16, the CPU 40, on receiving a command to start the measurement operations, initializes the various units (step S201). Specifically, the CPU 40 opens the 2-port valve 50, and closes the exhaust valve 32B and the exhaust valve 32C.

Next, the CPU 40 starts inflating the air bladder 25 for cuff wrapping by driving the inflation pump 31C (step S202).

Next, the CPU 40 judges whether wrapping of the cuff 20 around the upper arm after having completed inflation of the air bladder 25 for cuff wrapping has ended (step S203), and, if it is judged that wrapping of the cuff 20 has ended (if YES in step S203), starts inflating the air bladder 23 for pulse wave measurement and the air bladder 24 for blood pressure value measurement by driving the inflation pump 31B (step S204). The internal pressure of the air bladder 23 for pulse wave measurement and the internal pressure of the air bladder 24 for blood pressure value measurement will thereby respectively start to rise. In this inflation process, the CPU 40 acquires presure information for calculating blood pressure values such as maximum blood pressure and minimum blood pressure. Specifically, the CPU 40 acquires the pressure information based on a pressure signal input from the pressure sensor 33B.

Next, the CPU 40 judges whether blood pressure value measurement has ended (step S205), and, if it is judged that blood pressure value measurement has ended (if YES in step S205), starts pulse wave measurement (step S206). Specifically, the CPU 40 stops the drive of the inflation pump 31B, and then closes the 2-port valve 50. The internal pressure of the air bladder 23 for pulse wave measurement and the internal pressure of the air bladder 24 for blood pressure value measurement will thereby, respectively, be maintained at a higher pressure than maximum blood pressure at the point in time at which the drive of the inflation pump 31B is stopped, and the artery will be occluded at the fitting site on the upper arm. Subsequently, from the point in time at which the 2-port valve 50 is closed, the pulse wave transmitted via subcutaneous tissue from the portion of the artery adjacent to the proximal side end of the occluded artery will be sharply observed in the large-volume air bladder 24 for blood pressure value measurement and the small-volume air bladder 23 for pulse wave measurement that is cut off from the first piping portion L1 and the like connected to the large-volume air bladder 24 for blood pressure measurement. From the point in time at which the 2-port valve 50 is closed, the CPU 40 acquires the pulse wave based on the signal input from the pressure sensor 33A.

Next, the CPU 40 judges whether pulse wave measurement has ended (step S207), and, if it is judged that pulse wave measurement has ended (if YES in step S207), transitions to a stop operation (step S208). Specifically, the CPU 40 opens the 2-port valve 50, and also opens the exhaust valve 32B and the exhaust valve 32C. The internal pressure of the air bladder 23 for pulse wave measurement, the internal pressure of the air bladder 24 for blood pressure value measurement, and the internal pressure of the air bladder 25 for cuff wrapping thereby, respectively, start to fall at the point in time at which the exhaust valve 32B and the exhaust valve 32C are opened, and return to atmospheric pressure.

Next, the CPU 40 performs blood pressure value calculations and pulse wave analysis (step S209). Specifically, the CPU 40, respectively, calculates the maximum blood pressure, the minimum blood pressure, and an index indicating the degree of arteriosclerosis, based on the acquired pressure information and pulse waves.

Next, the CPU 40 displays the calculated maximum blood pressure, minimum blood pressure, and index indicating the degree of arteriosclerosis of the display unit 42. At this time, the CPU 40 may output the measurement results to the memory unit 41 and store the measurement results in the memory unit 41. After the measurement results are displayed, the test subject removes the upper arm from the hollow portion of the cuff 20. The series of measurement operations is ended as a result of the above, completing measurement of various types of blood pressure information using the blood pressure information measurement device 1C in the present embodiment.

Even with the blood pressure information measurement device 1C in the present embodiment described above, by providing the 2-port valve 50, the portion of the second piping portion L2 connecting the 2-port valve 50 and the air bladder 23 for pulse wave measurement, and the pressure sensor 33A provided on the second piping portion L2 all in the cuff 20, the volume of the enclosed space including the inner cavity 23c of the air bladder 23 for pulse wave measurement in which pressure detection is performed by the pressure sensor 33A at the time of pulse wave measurement is configured to be significantly smaller as compared with that in a conventional blood pressure information measurement device. Thus, even with the blood pressure information measurement device 1C in the present embodiment, fluctuations in pressure produced in the air bladder 23 for pulse wave measurement at the time of pulse wave measurement can be extremely sharply observed, enabling the S/N ratio of the pulse wave signal output from the pressure sensor 33A to be raised significantly as compared with that in a conventional blood pressure information measurement device. Accordingly, by adopting the blood pressure information measurement device 1C in the present embodiment, the pulse wave can be measured with high accuracy, and an index indicating the degree of arteriosclerosis can be calculated with maximum accuracy by computing the index indicating the degree of arteriosclerosis based on the obtained pulse wave.

Note that with the blood pressure information measurement device 1C in the abovementioned present embodiment, the case was illustrated where the cover portion 22b1 is provided at a prescribed position on the outer circumferential surface side of the outside shell 22b, and the 2-port valve 50 and the pressure sensor 33A are disposed inside the cover portion 22b1, but as long as the 2-port valve 50 and the pressure sensor 33A are provided in the cuff 20, the disposition position, method of fixing and the like are not particularly restricted.

Also, even with the blood pressure information measurement device 1C in the present embodiment, it is possible to apply a characteristic configuration like that applied to the blood pressure information measurement device according to the first modification or the second modification based on abovementioned Embodiment 1 of the present invention.

Also, although the case where air bladders in which compressed air is injected were employed as the air bladder 23 for pulse wave measurement, the air bladder 24 for blood pressure value measurement and the air bladder 25 for cuff wrapping was illustrated in the description of the abovementioned Embodiments 1 and 2 of the present invention and modifications thereof, it is naturally also possible to constitute these members with gas bags in which another gas is injected or liquid bags in which a liquid is injected.

Also, although the case where the air bladder 25 for cuff wrapping that compresses the curler 26 is employed as means for biasing the air bladder 23 for pulse wave measurement and the air bladder 24 for blood pressure value measurement toward the upper arm was illustrated in the description of the abovementioned Embodiment 2 of the present invention, various mechanisms, such as a belt rollup mechanism, can be employed as the biasing means.

Furthermore, although the case where one or more embodiments of the present invention are applied to a blood pressure information measurement device capable of acquiring maximum blood pressure, minimum blood pressure, and an index indicating the degree of arteriosclerosis was illustrated in the description of the abovementioned Embodiments 1 and 2 of the present invention and modifications thereof, as long as the blood pressure information measurement device is provided with at least a function of acquiring a pulse wave, one or more embodiments of the present invention can be applied to any device that acquires blood pressure information in addition to the above.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

REFERENCE NUMERALS LIST 1A-1C blood pressure information measurement device
10 main body
11 casing
20 cuff
21, 22 outer cover
21a inside cover
21b outside cover
22a inside cover
22b outside shell
22b1 cover portion
22c handle
23 air bladder for pulse wave measurement
23a inner circumferential portion
23b outer circumferential portion
23c inner cavity
24 air bladder for blood pressure value measurement
24a inner circumferential portion
24b outer circumferential portion
24c inner cavity
24d resin plate
24e fabric
25 air bladder for wrapping
25a inner circumferential portion
25b outer circumferential portion
25c inner cavity
26 curler
26a cloth bag
26b fabric
27 cover
28 cushion material
29A, 29B surface fastener
30B inflation/deflation mechanism
30C additional inflation/deflation mechanism
31B, 31C inflation pump
32B, 32C exhaust valve
33A-33C pressure sensor
36B, 36C inflation pump drive circuit
37B, 37C exhaust valve drive circuit
38A-38C amplifier
39A-39C A/D converter
40 CPU
41 memory unit
42 display unit
43 operating unit
50 2-port valve
51 2-port valve drive circuit
52 3-port valve
53 3-port valve drive circuit
60 connection cable
70 tube
100 left hand
101 upper arm
L1 first piping portion
L2 second piping portion
L3 third piping portion

The invention claimed is:

1. A blood pressure information measurement device comprising:
 a cuff that takes an annular form in a fitted state of being fitted on a fitting site;
 a first fluid bag that is provided in the cuff and is configured to be wrapped around a proximal side of the fitting site in the fitted state;
 a second fluid bag that is provided in the cuff and is configured to be wrapped around a portion including a distal side of the fitting site in the fitted state;
 a cushion material disposed between the first fluid bag and the second fluid bag;

an inflation and deflation mechanism that is capable of inflating and deflating the first fluid bag and the second fluid bag;

a main body that is separate from the cuff, and in which the inflation and deflation mechanism is provided;

a piping that connects the first fluid bag and the second fluid bag to the inflation and deflation mechanism, the piping comprising a first piping portion and a second piping portion, wherein the second piping portion is provided in the cuff and connects the first fluid ban and the second fluid bag through an opening/closing valve, and the first piping portion connects the second piping portion to the inflation and deflation mechanism;

the opening/closing valve that is provided in the piping, and that is set to an open state to allow communication of the first fluid bag with at least one of the second fluid bag and the inflation and deflation mechanism, and that is set to a closed state to maintain an internal pressure of the first fluid bag as it is by isolating the first fluid bag from the second fluid bag and the inflation and deflation mechanism;

a first pressure detection unit that is provided on the second piping portion and detects the internal pressure of the first fluid bag;

a pulse wave acquisition unit that acquires a pulse wave based on the pressure detected by the first pressure detection unit; and an index calculation unit that calculates an index indicating a degree of arteriosclerosis based on the pulse wave acquired by the pulse wave acquisition unit, wherein the opening/closing valve is provided in the cuff, wherein only one piping portion, which is the first piping portion, is provided between the cuff and the main body, wherein the first pressure detection unit is provided in the cuff, and wherein the cuff and the main body directly contact one another and are rotatably coupled.

2. The blood pressure information measurement device according to claim 1, wherein the piping comprises:

the first piping portion that connects the inflation and deflation mechanism and the second fluid bag; and the second piping portion that branches from the first piping portion, and connects the first piping portion and the first fluid bag, wherein the opening/closing valve consists of a 2-port valve provided in the second piping portion.

3. The blood pressure information measurement device according to claim 1, wherein the piping comprises:

the first piping portion that connects the inflation and deflation mechanism and the second fluid bag; and the second piping portion that branches from the first piping portion, and connects the first piping portion and the first fluid bag, wherein the opening/closing valve consists of a 3-port valve provided at a connection point of the first piping portion and the second piping portion.

4. The blood pressure information measurement device according to claim 1, further comprising:

a second pressure detection unit that detects an internal pressure of the second fluid bag; and a blood pressure value acquisition unit that acquires a blood pressure value based on the pressure detected by the second pressure detection unit.

5. The blood pressure information measurement device according to claim 1, wherein the second fluid bag covers an outer side of the first fluid bag, so as to be wrapped around substantially an entirety of the fitting site in the fitted state.

6. The blood pressure information measurement device according to claim 1, wherein the second fluid bag is disposed alongside the first fluid bag in an axial direction of the cuff, so as to be wrapped around only a portion excluding the proximal side of the fitting site in the fitted state.

7. The blood pressure information measurement device according to claim 1, wherein the cuff further comprises an outer body in which the first fluid bag and the second fluid bag are housed, wherein the opening/closing valve is housed in the outer body, wherein the portion of the piping connecting the first fluid bag and the opening/closing valve is housed in the outer body, and wherein the first pressure detection unit is housed in the outer body.

8. The blood pressure information measurement device according to claim 1, wherein the first piping portion connecting the cuff and the main body is constituted by a flexible tube.

9. The blood pressure information measurement device according to claim 1, further comprising:

a curved elastic board that is provided in the cuff, and is positioned on an outer side of the first fluid bag and the second fluid bag in the fitted state; and a third fluid bag that is provided in the cuff and is positioned on an outer side of the curve elastic board in the fitted state.

10. The blood pressure information measurement device according to claim 1, wherein the pulse wave acquisition unit acquires the pulse wave directly from the pressure detected by the first pressure detection unit.

11. The blood pressure information measurement device according to claim 1, wherein, in the fitted state, the cuff receives a piping connecting the cuff and the main body at an outer surface of the cuff.

* * * * *